(12) United States Patent
Shimojo et al.

(10) Patent No.: US 12,072,557 B2
(45) Date of Patent: Aug. 27, 2024

(54) OPHTHALMIC LENS, DESIGN METHOD FOR THE SAME, MANUFACTURING METHOD FOR THE SAME, AND OPHTHALMIC LENS SET

(71) Applicant: HOYA CORPORATION, Tokyo (JP)

(72) Inventors: Akira Shimojo, Tokyo (JP); Kazuo Nakazawa, Tokyo (JP)

(73) Assignee: HOYA CORPORATION, Tokyo (JP)

(*) Notice: Subject to any disclaimer, the term of this patent is extended or adjusted under 35 U.S.C. 154(b) by 702 days.

(21) Appl. No.: 17/284,727

(22) PCT Filed: Dec. 10, 2018

(86) PCT No.: PCT/JP2018/045234
§ 371 (c)(1),
(2) Date: Apr. 12, 2021

(87) PCT Pub. No.: WO2020/075312
PCT Pub. Date: Apr. 16, 2020

(65) Prior Publication Data
US 2021/0318556 A1 Oct. 14, 2021

(30) Foreign Application Priority Data
Oct. 11, 2018 (JP) .................... 2018-192437

(51) Int. Cl.
*G02C 7/06* (2006.01)
*G02C 7/04* (2006.01)

(52) U.S. Cl.
CPC ............. *G02C 7/06* (2013.01); *G02C 7/04* (2013.01)

(58) Field of Classification Search
CPC . G02C 7/06; G02C 7/04; G02C 7/042; G02C 7/044; G02C 7/047; G02C 7/041;
(Continued)

(56) References Cited

U.S. PATENT DOCUMENTS

| 6,322,213 B1 | 11/2001 | Altieri et al. |
| 6,709,103 B1 | 3/2004 | Roffman et al. |

(Continued)

FOREIGN PATENT DOCUMENTS

| EP | 2 988 161 A1 | 2/2016 |
| JP | 2002-503827 A | 2/2002 |

(Continued)

OTHER PUBLICATIONS

Apr. 8, 2021 International Preliminary Report on Patentability issued in International Patent Application No. PCT/JP2018/045234.
(Continued)

*Primary Examiner* — Joseph P Martinez
*Assistant Examiner* — Ray Alexander Dean
(74) *Attorney, Agent, or Firm* — Oliff PLC

(57) ABSTRACT

An ophthalmic lens and technologies relating to the ophthalmic lens including an intermediate portion that includes a portion in which a power is strengthened and thereafter weakened when the lens is viewed in an X direction from the center toward the periphery, and includes a portion A' in which the power is strengthened and thereafter weakened when the lens is viewed in an X' direction from the center toward the periphery, the X' direction being exactly opposite to the X direction, the power being strengthened in the portion A and the portion A' to be stronger than a far-vision power of a far-vision portion or a near-vision power of a near-vision portion that is arranged in a ring shape along an outer edge of the intermediate portion.

22 Claims, 18 Drawing Sheets

(58) Field of Classification Search
CPC .. A61F 2240/002; A61F 2/1618; G02B 1/043
See application file for complete search history.

(56) References Cited

U.S. PATENT DOCUMENTS

| | | |
|---|---|---|
| 2009/0303433 A1 | 12/2009 | Shimojo |
| 2010/0073629 A1 | 3/2010 | Menezes |
| 2010/0328604 A1 | 12/2010 | Collins et al. |
| 2016/0209677 A1 | 7/2016 | Izawa et al. |
| 2020/0004045 A1 | 1/2020 | Shimojyou et al. |

FOREIGN PATENT DOCUMENTS

| | | | | |
|---|---|---|---|---|
| JP | 2002503827 A | * | 2/2002 | |
| JP | 2006-505011 A | | 2/2006 | |
| JP | 2012-093522 A | | 5/2012 | |
| JP | 2012093522 A | * | 5/2012 | |
| JP | 6188974 B1 | * | 8/2017 | ............... G02C 7/04 |
| JP | 2018-120040 A | | 8/2018 | |
| WO | 00/08516 A1 | | 2/2000 | |
| WO | 2006/129707 A1 | | 12/2006 | |
| WO | 2015/041327 A1 | | 3/2015 | |

OTHER PUBLICATIONS

Mar. 12, 2019 International Search Report issued in International Patent Application No. PCT/JP2018/045234.
Jun. 10, 2022, Extended Search Report issued in European Patent Application No. 18936586.9.

\* cited by examiner

OPHTHALMIC LENS, DESIGN METHOD FOR THE SAME, MANUFACTURING METHOD FOR THE SAME, AND OPHTHALMIC LENS SET

TECHNICAL FIELD

The present invention relates to an ophthalmic lens, a design method for the same, a manufacturing method for the same, and an ophthalmic lens set.

BACKGROUND ART

Contact lenses and intraocular lenses are known as examples of ophthalmic lenses (in the present specification, spectacle lenses are excluded from ophthalmic lenses). For example, contact lenses include multifocal contact lenses (multifocal lenses) each having a near-vision power for seeing a near distance and a far-vision power for seeing a far distance with a single lens. An example configuration of such a multifocal lens is a configuration in which a near-vision portion having a near-vision power is arranged at the center of the lens, an intermediate portion in which the power changes is arranged in a ring shape along an outer edge of the near-vision portion, and a far-vision portion having a far-vision power is arranged in a ring shape along an outer edge of the intermediate portion (e.g., FIGS. 1 and 2 of Patent Document 1). Conversely, a configuration is also known in which a far-vision portion having a far-vision power is arranged at the center of the lens, an intermediate portion in which the power changes is arranged in a ring shape along an outer edge of the far-vision portion, and a near-vision portion having a near-vision power is arranged in a ring shape along an outer edge of the intermediate portion (e.g., FIG. 12 of Patent Document 2).

CITATION LIST

Patent Documents

Patent Document 1: JP 2006-505011A
Patent Document 2: WO 2006/129707

SUMMARY OF INVENTION

Technical Problem

Before describing a problem to be solved by the present invention, an optical portion will be described. Note that the following describes, merely as an example, a multifocal contact lens (a multifocal lens, also simply referred to as a "lens") in which a near-vision portion having a near-vision power is arranged at the center of the lens, an intermediate portion in which the power changes is arranged in a ring shape along an outer edge of the near-vision portion, and a far-vision portion having a far-vision power is arranged in a ring shape along an outer edge of the intermediate portion.

FIG. 1 is a schematic diagram showing a conventional multifocal lens in a plan view.

In FIG. 1, the lens is viewed from above in an optical axis direction in a state where the lens is placed on a horizontal table with a front surface (a convex surface) of the lens facing upward. This similarly applies hereinafter with respect to plan views. A distance between points on the lens in the plan view will be referred to as a "plan view distance". The reference sign 1 denotes the near-vision portion, the reference sign 2 denotes the far-vision portion, the reference sign 3 denotes the intermediate portion, the reference sign 4 denotes an optical portion, the reference sign 5 denotes a peripheral portion, and the reference sign 6 denotes the multifocal contact lens. The reference signs are omitted in the following description.

As shown in FIG. 1, the near-vision portion is arranged at the center, the annular intermediate portion is arranged along an outer edge of the near-vision portion, and the far-vision portion is arranged along an outer edge of the intermediate portion such that the near-vision portion, the intermediate portion, and the far-vision portion have a common center that is an optical center O of the lens. In this example, the optical center O matches a geometric center. Thus, the optical portion that includes the near-vision portion, the intermediate portion, and far-vision portion is configured. The lens further includes an annular peripheral portion along an outer edge of the optical portion. The peripheral portion usually has a flange shape so that the peripheral portion can easily enter the back side of an eyelid when the lens is placed on a cornea. That is, the lens of this example is constituted by the optical portion and the peripheral portion. However, the optical portion and the peripheral portion are distinguished from each other because the optical portion and the peripheral portion respectively have the functions described above, and there is no clear boundary that can be visually recognized such as a step between the optical portion and the peripheral portion.

The following describes a problem to be solved by the present invention.

A spherical power referred to in the present specification means an average value of a refractive power in a direction from the center of the lens toward the periphery, i.e., a radial direction (also called a meridional direction or a tangential direction) and a refractive power in a direction perpendicular to the radial direction, i.e., a circumferential direction (a sagittal direction). A plot of the spherical power is also referred to as a "power distribution". Also, in the following description, the spherical power will be also referred to as a "far-vision power" or simply a "power". Power plots referred to in the present specification are obtained by adjusting the shape of a front surface while forming a rear surface as a spherical surface.

FIG. 2 is a diagram obtained by plotting the power of a conventional multifocal contact lens (with near-vision center) from an end $F_2$ to an end $F_2'$ of an optical portion in an X-X' direction. The far-vision power (spherical power) S is set to 0 D (unit: diopter [D]), the near-vision power (S+ADD) is set to +2.00 D, and an astigmatic power C is set to 0 D. That is, an additional power ADD of the conventional lens is +2.00 D. In the present specification, an "additional power" refers to a value obtained by subtracting a far-vision power from a near-vision power. The horizontal axis indicates a distance (unit: mm) from the optical center O in the X-X' direction in a plan view of the lens. The vertical axis indicates the spherical power (unit: diopter [D]) of the lens. This similarly applies hereinafter with respect to diagrams obtained by plotting spherical powers.

Note that optical design analysis software (Zemax OpticStudio: manufactured by Zemax, LLC) in which ray tracing is used was used to obtain the plot shown in FIG. 2. An aperture diameter was set to 8.0 mm, and the wavelength of light was set to 550 nm. This similarly applies hereinafter in the present specification unless otherwise stated.

Incidentally, in this conventional lens, a near-vision portion is arranged at the center and a far-vision portion is arranged in a ring shape along an outer edge of an intermediate portion. A lens of this type will hereinafter be referred to as a "lens with near-vision center". To the contrary, a lens in which a far-vision portion is arranged at the center and a near-vision portion is arranged in a ring shape along an outer edge of an intermediate portion will be referred to as a "lens with far-vision center".

FIG. 3 is a diagram obtained by plotting a cylinder power of the lens shown in FIG. 2 from the end $F_2$ to the end $F_2'$ of the optical portion in the X-X' direction. The horizontal axis indicates a distance (unit: mm) from the optical center O in the X-X' direction in a plan view of the lens. The vertical axis indicates the cylinder power (unit: diopter [D]). This similarly applies hereinafter with respect to diagrams obtained by plotting cylinder powers.

In the present specification, "cylinder power" indicates the magnitude of astigmatism. The "astigmatism" refers to an absolute value of a difference between a power in the meridional direction or the tangential direction (an X direction and an X' direction, which will be described later) and a power in the sagittal direction. A large cylinder power makes an image that is viewed by a wearer of the lens obscure.

In FIGS. 2 and 3, $F_2$-$F_1$ and $F_2'$-$F_1'$ correspond to the far-vision portion, $F_1$-N and $F_1'$-N' correspond to the intermediate portion, and N-N' corresponds to the near-vision portion.

In the conventional lens, the power decreases from the near-vision power toward the far-vision power in a direction from the center toward the periphery of the lens. With this change in the power, a cylinder power is generated (points indicated by arrows α and α' in FIG. 3). The cylinder power is considered to decrease in the far-vision portion in which the change in the power is small. However, the inventor of the present invention found that this is not true in the conventional lens (points indicated by arrows ß and ß' in FIG. 3).

More specifically, the inventor of the present invention found that, when the lens is viewed from the center toward the periphery (hereinafter also simply referred to as "in the radial direction"), the cylinder power generated in the intermediate portion does not immediately decrease across the intermediate portion to the far-vision portion, and there is a relatively large cylinder power even in the far-vision portion provided along the outer edge of the intermediate portion.

A large cylinder power is one cause of an image being obscure. Therefore, it is preferable to secure a wide region in which the cylinder power is small in the far-vision portion provided along the outer edge.

A problem to be solved by the present invention is to secure a wide region in which the cylinder power is small in a far-vision portion or a near-vision portion that is provided along the outer edge of the intermediate portion.

Solution to Problem

The inventor of the present invention considered reasons why the cylinder power generated in the intermediate portion does not immediately decrease in the conventional lens.

One reason is that the near-vision portion, the intermediate portion, and the far-vision portion are concentrically formed in the conventional multifocal contact lens shown in FIG. 1.

That is, there is a high degree of freedom in changing the curvature in the radial (meridional) direction from the center toward the periphery in a multifocal contact lens. Therefore, the power can be changed across the near-vision portion, the intermediate portion, and the far-vision portion.

On the other hand, when compared to the radial direction, there is little freedom to change the curvature in the circumferential (sagittal) direction that is perpendicular to the radial direction. This is because there is a restriction in which the near-vision portion, the intermediate portion, and the far-vision portion are to be concentrically formed and a continuous lens surface (a smooth lens surface) is to be formed.

When the lens is viewed from the center toward the periphery, in the near-vision portion arranged at the center of the lens, a shape that is close to a spherical surface can be maintained, a difference between the curvature in the radial direction and the curvature in the circumferential direction is small, and the cylinder power is accordingly small.

However, in the intermediate portion in which the power changes, the curvature in the radial direction changes from the center toward the periphery similarly to the power, but the curvature in the circumferential direction does not change much from the curvature in the near-vision portion. This tendency is maintained even in the far-vision portion past the intermediate portion. Therefore, in the conventional lens, a divergence between the curvature in the radial direction and the curvature in the circumferential direction (i.e., a cylinder power) is generated, and the divergence is kept large even in the far-vision portion. As a result, the cylinder power generated in the intermediate portion does not immediately decrease and remains even in the far-vision portion in which the change in the power is small.

Based on the findings described above, the inventor of the present invention performed intensive studies. As a result, the inventor arrived at a method of reducing (or increasing if the far-vision portion is arranged at the center) the power from the center toward the periphery in the intermediate portion by an amount larger than an additional power set for the lens, and thereafter increasing (or reducing if the far-vision portion is arranged at the center) the power in the intermediate portion.

With this method, in a case where the near-vision portion is arranged at the center of the lens and the far-vision portion is arranged along the outer edge of the intermediate portion arranged along the outer edge of the near-vision portion, not only the curvature in the radial direction largely decreases but also the curvature in the circumferential direction relatively largely decreases as a result of the power being reduced by an amount larger than the additional power set for the lens. As a result of the power being increased thereafter, the curvature in the radial direction increases but the curvature in the circumferential direction does not change much, and thus it is possible to reduce the difference between the curvature in the radial direction and the curvature in the circumferential direction.

To the contrary, in a case where the far-vision portion is arranged at the center of the lens and the near-vision portion is arranged along the outer edge of the intermediate portion arranged along the outer edge of the far-vision portion, not only the curvature in the radial direction largely increases but also the curvature in the circumferential direction relatively largely increases as a result of the power being increased by an amount larger than the additional power set for the lens. As a result of the power being reduced thereafter, the curvature in the radial direction decreases but the curvature in the circumferential direction does not change much, and thus it is possible to reduce the difference between the curvature in the radial direction and the curvature in the circumferential direction.

That is, with the method described above, it is possible to make the curvature in the circumferential direction closer to the curvature in the radial direction. Thus, the cylinder power can be made 0 or close to 0 in the portion (e.g., the far-vision portion) provided along the outer edge.

Based on the findings described above, the following configurations of the present invention are adopted. Note that preferable aspects described below can be combined as appropriate.

A first aspect of the present invention is an ophthalmic lens including an optical portion that includes a near-vision portion having a near-vision power that corresponds to a near distance, a far-vision portion having a far-vision power that corresponds to a distance that is farther than the near distance, and an annular intermediate portion that connects the near-vision portion and the far-vision portion to each other, the near-vision portion or the far-vision portion being arranged close to the center, the near-vision portion or the far-vision portion that is not arranged close to the center being arranged in a ring shape along an outer edge of the intermediate portion, wherein the intermediate portion includes a portion A in which a power is strengthened and thereafter weakened when the lens is viewed in an X direction from the center toward the periphery, and the intermediate portion includes a portion A in which the power is strengthened and thereafter weakened when the lens is viewed in an X' direction from the center toward the periphery, the X' direction being exactly opposite to the X direction, the power being strengthened in the portion A and the portion A' to be stronger than the far-vision power of the far-vision portion that is arranged in the ring shape along the outer edge of the intermediate portion or the near-vision power of the near-vision portion that is arranged in the ring shape along the outer edge of the intermediate portion.

In a second aspect of the present invention that is an aspect of the first aspect, in the optical portion, the far-vision portion is arranged in the ring shape along the outer edge of the intermediate portion, and the lens has a shape with which the power is strengthened for far vision to be stronger than the far-vision power and thereafter weakened to reach the far-vision power in the X direction in the portion A and in the X' direction in the portion A'.

In a third aspect of the present invention that is an aspect of the second aspect, when the lens is viewed in the X direction and the X' direction, a cylinder power (unit: diopter) satisfies the following conditions, cylinder power at a point at which the power reaches the far-vision power as a result of being weakened after being strengthened for far vision to be stronger than the far-vision power in the portion A≤0.30 D,  Condition 1-1 cylinder power at a point at which the power reaches the far-vision power as a result of being weakened after being strengthened for far vision to be stronger than the far-vision power in the portion A'≤0.30 D.  Condition 2-1

In a fourth aspect of the present invention that is an aspect of the second or third aspect, a ratio of a difference between each local minimum power value in the portion A and the portion A' and the far-vision power to a difference between the near-vision power and the far-vision power is at least 0.15 and no greater than 1.0.

In a fifth aspect of the present invention that is an aspect of the first aspect, in the optical portion, the near-vision portion is arranged in the ring shape along the outer edge of the intermediate portion, and the lens has a shape with which the power is strengthened for near vision to be stronger than the near-vision power and thereafter weakened to reach the near-vision power in the X direction in the portion A and in the X' direction in the portion A'.

In a sixth aspect of the present invention that is an aspect of the fifth aspect, when the lens is viewed in the X direction and the X' direction, a cylinder power (unit: diopter) satisfies the following conditions, cylinder power at a point at which the power reaches the near-vision power as a result of being weakened after being strengthened for near vision to be stronger than the near-vision power in the portion A≤0.30 D, and  Condition 1-2 cylinder power at a point at which the power reaches the near-vision power as a result of being weakened after being strengthened for near vision to be stronger than the near-vision power in the portion A'≤0.30 D.  Condition 2-2

In a seventh aspect of the present invention that is an aspect of the fifth or eighth aspect, a ratio of a difference between each local maximum power value in the portion A and the portion A' and the near-vision power to a difference between the near-vision power and the far-vision power is at least 0.15 and no greater than 1.0.

In an eighth aspect of the present invention that is an aspect of any one of the first to seventh aspects, the near-vision portion or the far-vision portion that is arranged at the center is provided so as to include an optical center of the ophthalmic lens.

In a ninth aspect of the present invention that is an aspect of any one of the first to eighth aspects, the ophthalmic lens is a contact lens.

In a tenth aspect of the present invention that is an aspect of any one of the first to eighth aspects, the ophthalmic lens is an intraocular lens.

An eleventh aspect of the present invention is a method for designing an ophthalmic lens that includes an optical portion that includes a near-vision portion having a near-vision power that corresponds to a near distance, a far-vision portion having a far-vision power that corresponds to a distance that is farther than the near distance, and an annular intermediate portion that connects the near-vision portion and the far-vision portion to each other, the near-vision portion or the far-vision portion being arranged close to the center, the near-vision portion or the far-vision portion that is not arranged close to the center being arranged in a ring shape along an outer edge of the intermediate portion, the method including:

designing the ophthalmic lens such that the intermediate portion includes a portion A in which a power is strengthened and thereafter weakened when the lens is viewed in an X direction from the center toward the periphery, and the intermediate portion includes a portion A' in which the power is strengthened and thereafter weakened when the lens is viewed in an X' direction from the center toward the periphery, the X' direction being exactly opposite to the X direction, the power being strengthened in the portion A and the portion A' to be stronger than the far-vision power of the far-vision portion that is arranged in the ring shape along the outer edge of the intermediate portion or the near-vision power of the near-vision portion that is arranged in the ring shape along the outer edge of the intermediate portion.

In a twelfth aspect of the present invention that is an aspect of the eleventh aspect, in the optical portion, the far-vision portion is arranged in the ring shape along the outer edge of the intermediate portion, and the ophthalmic lens is designed such that the power is strengthened for far vision to be stronger than the far-vision power and thereafter weakened to reach the far-vision power in the X direction in the portion A and in the X' direction in the portion A'.

In a 13th aspect of the present invention that is an aspect of the twelfth aspect, when the lens is viewed in the X direction and the X' direction, a cylinder power (unit: diopter) satisfies the following conditions, cylinder power at a point at which the power reaches the far-vision power as a result of being weakened after being strengthened for far vision to be stronger than the far-vision power in the portion A≤0.30 D,     Condition 1-1 cylinder power at a point at which the power reaches the far-vision power as a result of being weakened after being strengthened for far vision to be stronger than the far-vision power in the portion A'≤0.30 D.     Condition 2-1

In a 14th aspect of the present invention that is an aspect of the twelfth or 13th aspect, a ratio of a difference between each local minimum power value in the portion A and the portion A' and the far-vision power to a difference between the near-vision power and the far-vision power is at least 0.15 and no greater than 1.0.

In a 15th aspect of the present invention that is an aspect of the eleventh aspect, in the optical portion, the near-vision portion is arranged in the ring shape along the outer edge of the intermediate portion, and the ophthalmic lens is designed such that the power is strengthened for near vision to be stronger than the near-vision power and thereafter weakened to reach the near-vision power in the X direction in the portion A and in the X' direction in the portion A'.

In a 16th aspect of the present invention that is an aspect of the 15th aspect, when the lens is viewed in the X direction and the X' direction, a cylinder power (unit: diopter) satisfies the following conditions, cylinder power at a point at which the power reaches the near-vision power as a result of being weakened after being strengthened for near vision to be stronger than the near-vision power in the portion A≤0.30 D, and     Condition 1-2 cylinder power at a point at which the power reaches the near-vision power as a result of being weakened after being strengthened for near vision to be stronger than the near-vision power in the portion A'≤0.30 D.     Condition 2-2

In a 17th aspect of the present invention that is an aspect of the 15th or 16th aspect, a ratio of a difference between each local maximum power value in the portion A and the portion A' and the near-vision power to a difference between the near-vision power and the far-vision power is at least 0.15 and no greater than 1.0.

In an 18th aspect of the present invention that is an aspect of any one of the eleventh to 17th aspects, the near-vision portion or the far-vision portion that is arranged at the center is provided so as to include an optical center of the ophthalmic lens.

In a 19th aspect of the present invention that is an aspect of any one of the eleventh to 18th aspects, the ophthalmic lens is a contact lens.

In a 20th aspect of the present invention that is an aspect of any one of the eleventh to 18th aspects, the ophthalmic lens is an intraocular lens.

A 21st aspect of the present invention is a method for manufacturing an ophthalmic lens, including:

a design step of designing an ophthalmic lens using the method for designing an ophthalmic lens according to any one of the eleventh to 20th aspects; and a processing step of manufacturing the designed ophthalmic lens using a processing device.

Aspects of an ophthalmic lens set that includes a plurality of the above-described ophthalmic lenses are listed below. Note that aspects in which any of the above-described preferable aspects are combined as appropriate with the following aspects are also aspects of the present invention.

A 22nd aspect of the present invention is an ophthalmic lens set including a plurality of ophthalmic lenses that each include an optical portion that includes a near-vision portion having a near-vision power that corresponds to a near distance, a far-vision portion having a far-vision power that corresponds to a distance that is farther than the near distance, and an annular intermediate portion that connects the near-vision portion and the far-vision portion to each other, the near-vision portion or the far-vision portion being arranged close to the center, the near-vision portion or the far-vision portion that is not arranged close to the center being arranged in a ring shape along an outer edge of the intermediate portion, wherein the intermediate portion includes a portion A in which a power is strengthened and thereafter weakened when the lens is viewed in an X direction from the center toward the periphery, and the intermediate portion includes a portion A' in which the power is strengthened and thereafter weakened when the lens is viewed in an X' direction from the center toward the periphery, the X' direction being exactly opposite to the X direction, the power being strengthened in the portion A and the portion A' to be stronger than the far-vision power of the far-vision portion that is arranged in the ring shape along the outer edge of the intermediate portion or the near-vision power of the near-vision portion that is arranged in the ring shape along the outer edge of the intermediate portion.

Other aspects that can be combined with the above-described aspects are listed below.

In a 23rd aspect of the present invention that is an aspect of each of the above-described aspects, in the optical portion, the near-vision portion is arranged close to the center, and the portions A and A' are portions in the intermediate portion in which, after the power has decreased, the power (preferably, monotonously) decreases to be smaller than the far-vision power, and thereafter again (preferably, monotonously) increases up to the far-vision power when the portion A is viewed in the X direction, for example.

In a 24th aspect of the present invention that is an aspect of the 23rd aspect, the power has a local minimum value only at a point in the portion A and has a local minimum value only at a point in the portion A'.

In a 25$^{th}$ aspect of the present invention that is an aspect of the 23$^{rd}$ or 24$^{th}$ aspect, a plan view distance L between a point at which the power has a local minimum value in the portion A and a point at which the power has a local minimum value in the portion A' is preferably 2.0 to 5.0 mm. The lower limit is more preferably 2.2 mm, and the upper limit is more preferably 4.8 mm.

In a 26$^{th}$ aspect of the present invention that is an aspect of any one of the 23$^{rd}$ to 25$^{th}$ aspects, a ratio of a difference between each local minimum power value in the portion A and the portion A' and the far-vision power to a difference between the near-vision power and the far-vision power is preferably at least 0.15 and no greater than 1.0. The lower limit of the ratio is more preferably 0.25, further preferably 0.30, and particularly preferably 0.40, and the upper limit of the ratio is more preferably 0.90, further preferably 0.80, and particularly preferably 0.70.

In a 27$^{th}$ aspect of the present invention that is an aspect of any one of the 23$^{rd}$ to 26$^{th}$ aspects, when a straight line X-X' is rotated relative to the lens about an optical center O from 0° to 180°, a portion of the far-vision portion in which the cylinder power is no greater than 0.50 D is preferably at least 80 area %, more preferably at least 90 area %, and further preferably at least 95 area %.

In a 28$^{th}$ aspect of the present invention that is an aspect of any one of the 23$^{rd}$ to 27$^{th}$ aspects, the far-vision portion is preferably within a range of ±0.50 D (preferably ±0.25 D) with respect to the far-vision power.

In a 29$^{th}$ aspect of the present invention that is an aspect of any one of the 23$^{rd}$ to 28$^{th}$ aspects, the near-vision portion is preferably within a range of ±0.50 D (preferably ±0.25 D) with respect to the near-vision power. The near-vision portion is further preferably within a range of +0.50 D (preferably +0.25 D) with respect to the near-vision power.

In a 30$^{th}$ aspect of the present invention that is an aspect of each of the above-described aspects, in the optical portion, the far-vision portion is arranged close to the center, and the portions A and A' are portions in the intermediate portion in which, after the power has increased, the power (preferably, monotonously) increases to be larger than the near-vision power, and thereafter again (preferably, monotonously) decreases to reach the near-vision power when the portion A is viewed in the X direction, for example.

In a 31$^{st}$ aspect of the present invention that is an aspect of the 30$^{th}$ aspect, the power has a local maximum value only at a point in the portion A and has a local maximum value only at a point in the portion A'.

In a 32$^{nd}$ aspect of the present invention that is an aspect of the 30$^{th}$ or 31$^{st}$ aspect, the plan view distance L is preferably 2.0 to 5.0 mm. The lower limit is more preferably 2.2 mm, and the upper limit is more preferably 4.8 mm.

In a 33$^{rd}$ aspect of the present invention that is an aspect of any one of the 30$^{th}$ to 32$^{nd}$ aspects, a ratio of a difference between each local maximum power value in the portion A and the portion A' and the near-vision power to a difference between the near-vision power and the far-vision power is preferably at least 0.15 and no greater than 1.0. The lower limit of the ratio is more preferably 0.25, further preferably 0.30, and particularly preferably 0.40, and the upper limit of the ratio is more preferably 0.90, further preferably 0.80, and particularly preferably 0.70.

In a 34$^{th}$ aspect of the present invention that is an aspect of any one of the 30$^{th}$ to 33$^{rd}$ aspects, when a straight line X-X' is rotated relative to the lens about an optical center O from 0° to 180°, a portion of the far-vision portion in which the cylinder power is no greater than 0.50 D is preferably at least 80 area %, more preferably at least 90 area %, and further preferably at least 95 area %.

In a 35$^{th}$ aspect of the present invention that is an aspect of any one of the 30$^{th}$ to 34$^{th}$ aspects, the far-vision portion is preferably within a range of ±0.50 D (preferably ±0.25 D) with respect to the far-vision power.

In a 36$^{th}$ aspect of the present invention that is an aspect of any one of the 30$^{th}$ to 35$^{th}$ aspects, the near-vision portion is preferably within a range of ±0.50 D (preferably −0.50 D, and further preferably −0.25 D) with respect to the near-vision power.

The conditions 1-1 and 2-1 described above may also be replaced with the following conditions 1'-1 and 2'-1 or may also be added to conditions 1 and 2.

[cylinder power (indicated by an arrow β in FIG. 5) at a point at which the power reaches the far-vision power as a result of being weakened after being strengthened for far vision to be stronger than the far-vision power in the portion A]/[maximum cylinder power (indicated by an arrow α in FIG. 5) in the intermediate portion] ≤0.30 (preferably ≤0.25, more preferably ≤0.20, and further preferably ≤0.15)     Condition 1'-1

[cylinder power (indicated by an arrow β' in FIG. 5) at a point at which the power reaches the far-vision power as a result of being weakened after being strengthened for far vision to be stronger than the far-vision power in the portion A']/[maximum cylinder power (indicated by an arrow α' in FIG. 5) in the intermediate portion] ≤0.30 (preferably ≤0.25, more preferably ≤0.20, and further preferably ≤0.15)     Condition 2'-1

The conditions 1-2 and 2-2 described above may also be replaced with the following conditions 1'-2 and 2'-2 or may also be added to conditions 1 and 2.

[cylinder power (indicated by an arrow β in FIG. 5) at a point at which the power reaches the near-vision power as a result of being weakened after being strengthened for near vision to be stronger than the near-vision power in the portion A]/[maximum cylinder power (indicated by an arrow α in FIG. 5) in the intermediate portion]≤0.30 (preferably ≤0.25, more preferably ≤0.20, and further preferably ≤0.15)     Condition 1'-2

[cylinder power (indicated by an arrow β' in FIG. 5) at a point at which the power reaches the near-vision power as a result of being weakened after being strengthened for near vision to be stronger than the near-vision power in the portion A']/[maximum cylinder power (indicated by an arrow α' in FIG. 5) in the intermediate portion]≤0.30 (preferably ≤0.25, more preferably ≤0.20, and further preferably ≤0.15)     Condition 2'-2

There is also the following aspect.

An ophthalmic lens, a design method, or a manufacturing method for the same, the ophthalmic lens including an optical portion that includes a near-vision portion having a near-vision power that corresponds to a near distance, a far-vision portion having a far-vision power that corresponds to a distance that is farther than the near distance, and an annular intermediate portion that connects the near-vision portion and the far-vision portion to each other, the near-vision portion or the far-vision portion being arranged close to the center, the near-vision portion or the far-vision portion that is not arranged close to the center being arranged in a ring shape along an outer edge of the intermediate portion, wherein the far-vision portion or the near-vision portion that is arranged in the ring shape along an outer edge of a center portion of the optical portion includes a portion A in which a power is strengthened and thereafter weakened when the lens is viewed in an X direction from the center toward the periphery, and includes an inflection point of the power when the lens is viewed in an X' direction from the center toward the periphery, the X' direction being exactly opposite to the X direction.

There is also the following aspect.

An ophthalmic lens including an optical portion that includes a near-vision portion having a near-vision power that corresponds to a near distance, a far-vision portion having a far-vision power that corresponds to a distance that is farther than the near distance, and an annular intermediate portion that connects the near-vision portion and the far-vision portion to each other, the near-vision portion or the far-vision portion being arranged close to the center, the near-vision portion or the far-vision portion that is not arranged close to the center being arranged in a ring shape along an outer edge of the intermediate portion, wherein in the intermediate portion, a curvature in a circumferential direction is made closer to a curvature in a radial direction when the lens is viewed in an X direction from the center toward the periphery, and the curvature in the circumferential direction is made closer to the curvature in the radial direction when the lens is viewed in an X' direction from the center toward the periphery, the X' direction being exactly opposite to the X direction.

There is also the following aspect.

An ophthalmic lens including an optical portion that includes a near-vision portion having a near-vision power that corresponds to a near distance, a far-vision portion having a far-vision power that corresponds to a distance that is farther than the near distance, and an annular intermediate portion that connects the near-vision portion and the far-vision portion to each other, the near-vision portion or the far-vision portion being arranged close to the center, the near-vision portion or the far-vision portion that is not arranged close to the center being arranged in a ring shape along an outer edge of the intermediate portion, wherein in a case where the far-vision portion is arranged in the ring shape along the outer edge of the intermediate portion in the optical portion, a cylinder power (unit: diopter) satisfies the following condition 1 when the lens is viewed in an X direction from the center toward the periphery and an X' direction from the center toward the periphery, the X' direction being exactly opposite to the X direction, cylinder power at a point at which the power reaches the far-vision power as a result of being weakened after being strengthened for far vision to be stronger than the far-vision power in the intermediate portion≤0.30 D, and    Condition 1 in a case where the near-vision portion is arranged in the ring shape along the outer edge of the intermediate portion in the optical portion, the cylinder power satisfies the following condition 2 when the lens is viewed in the X direction and the X' direction, cylinder power at a point at which the power reaches the near-vision power as a result of being weakened after being strengthened for near vision to be stronger than the near-vision power in the intermediate portion≤0.30 D.    Condition 2

The conditions 1 and 2 in the configuration described above may also be replaced with the following conditions 1' and 2', or the following conditions 1' and 2' may also be added to the conditions 1 and 2.

[cylinder power at a point at which the power reaches the far-vision power as a result of being weakened after being strengthened for far vision to be stronger than the far-vision power in the intermediate portion]/[maximum cylinder power in the intermediate portion]≤0.30    Condition 1'

[cylinder power at a point at which the power reaches the near-vision power as a result of being weakened after being strengthened for near vision to be stronger than the near-vision power in the intermediate portion]/[maximum cylinder power in the intermediate portion] ≤0.30    Condition 2'

Advantageous Effects of Invention

According to the present invention, it is possible to secure a wide region in which the cylinder power is small in the far-vision portion or the near-vision portion that is arranged along the outer edge of the intermediate portion.

DESCRIPTION OF EMBODIMENTS

Figure 1:
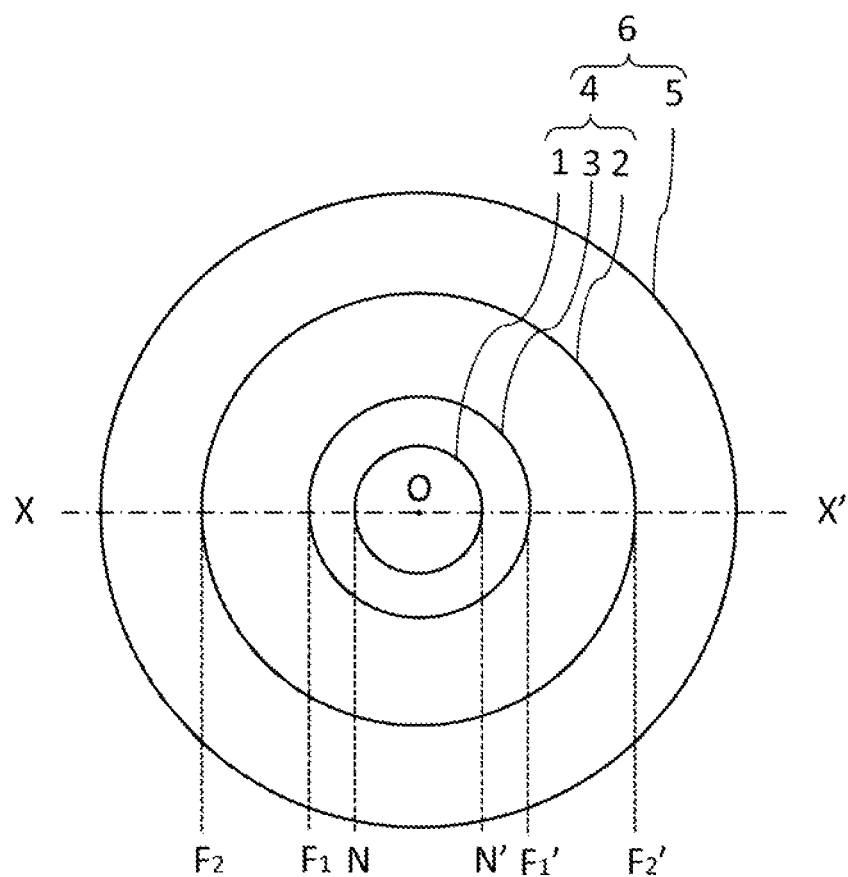
FIG. 1 is a schematic diagram showing a conventional multifocal lens in a plan view.

The following is a detailed description of an embodiment of the present invention with reference to the drawings.

The present embodiment will be described in the order shown below.

1. Contact lens
1-1. Multifocal contact lens (multifocal lens)
1-1-1. Near-vision portion arranged at the center and far-vision portion arranged in ring shape along outer edge of intermediate portion
1-1-2. Far-vision portion arranged at the center and near-vision portion arranged in ring shape along outer edge of intermediate portion
1-2. Other contact lenses
2. Design method (manufacturing method) for contact lens
3. Intraocular lens (IOL) and design method (manufacturing method) for the same
4. Ophthalmic lens set
5. Variations Note that known configurations may be adopted as appropriate for configurations that are not described below. Also, in the present specification, "to" between numerical values means being greater than or equal to a predetermined numerical value and less than or equal to a predetermined numerical value.

Also, each ophthalmic lens (a contact lens or a lens body of an intraocular lens) referred to in the present specification has two mutually opposite surfaces. A surface that is located on a retina side when the ophthalmic lens is worn by a wearer will be referred to as a "rear surface" and a surface that is located on an object side that is opposite to the retina side will be referred to as a "front surface".

Also, in the present specification, the term "power" refers to an optical power (unit: diopter [D]).

In the present specification, in cases where a near-vision portion is arranged at the center and a far-vision portion is arranged in a ring shape along an outer edge of a center portion, "strengthening a far-vision power" in the far-vision portion means strengthening the power in a direction that makes it possible to see a farther distance, i.e., in the minus direction, and means reducing the power (e.g., 0.00 D→−0.10 D). To the contrary, "weakening the far-vision power" means weakening the power in a direction that makes it difficult to see a far distance, i.e., in the plus direction, and means increasing the power (e.g., −0.10 D→0.00 D).

On the other hand, in cases where a far-vision portion is arranged at the center and a near-vision portion is arranged in a ring shape along an outer edge of a center portion, "strengthening a near-vision power" in the near-vision portion means strengthening the power in a direction that makes it possible to see a nearer distance, i.e., in the plus direction, and means increasing the power (e.g., 5.00 D→5.10 D). To the contrary, "weakening the near-vision power" means weakening the power in a direction that makes it difficult to see a near distance, i.e., in the plus direction, and means reducing the power (e.g., 5.10 D→5.00 D).

That is, in a case where which of the far-vision portion and the near-vision portion is to be arranged along the outer edge of the center portion is not determined yet, "strengthening the power" means strengthening the far-vision power or the near-vision power, and "weakening the power" means weakening the far-vision power or the near-vision power.

1. Contact Lens 1-1. Multifocal Contact Lens (Multifocal Lens)

In the present embodiment, a multifocal contact lens (a multifocal lens, hereinafter also simply referred to as a "lens") will be mainly described as an example.

1-1-1. Near-Vision Portion Arranged at the Center and Far-Vision Portion Arranged in Ring Shape Along Outer Edge of Center Portion Similarly to the conventional lens described above, a lens in the present embodiment includes a substantially circular optical portion that mainly contributes to optical performance and an annular peripheral portion that is located along a peripheral edge of the optical portion.

As described above, the peripheral portion usually has a flange shape so that the peripheral portion can easily enter the back side of an eyelid when the lens is placed on a cornea.

The optical portion includes a near-vision portion that has a near-vision power for seeing a near distance, a far-vision portion that has a far-vision power for seeing a distance (including infinity) that is farther than the near distance, and an annular intermediate portion that connects the near-vision portion and the far-vision portion to each other. Note that the intermediate portion is a region in which the power continuously changes, the curvature in the radial direction and the curvature in the circumferential direction continuously change, and there is no step in a lens surface.

Note that there is no particular limitation on the near distance referred to in the present specification so long as the near distance is nearer than a far distance. Of course, the near distance may also be an absolute distance (e.g., 100 cm or less, or 40 cm, which is a reading distance, or less) that is near.

In an example described in the present embodiment, the near-vision portion is arranged at the center, the annular intermediate portion is arranged along an outer edge of the near-vision portion, and the far-vision portion is arranged in a ring shape along an outer edge of the intermediate portion. Note that the configuration in a plan view is similar to that shown in FIG. 1 described above. In this example as well, the optical center O matches the geometric center of the lens, but the present invention is not limited to such a configuration (this similarly applies hereinafter).

As described above, in the lens according to the present embodiment, the near-vision portion is arranged at the center, the annular intermediate portion is arranged along the outer edge of the near-vision portion, and the far-vision portion is arranged in the ring shape along the outer edge of the intermediate portion. Accordingly, the power at the optical center O is set to be higher than the power in the far-vision portion. In the present specification, "the power being high" means the value of the power being large. This similarly applies hereinafter with respect to "high" and "low" regarding the power.

Note that values of the far-vision power S and the additional power ADD (and the astigmatic power C in cases where astigmatism is corrected) are usually given as a prescription of a lens, and the near-vision power is a value "S+ADD" (the unit of each power is [D], this similarly applies hereinafter). In the near-vision portion N-N', a power in the vicinity of the optical center O is taken to be the value of the near-vision power. Note that it is also possible to set the power at the position of the optical center O to the value of the near-vision power (i.e., power at the optical center O=near-vision power), and if the optical center O is shifted from the geometric center, the power at the geometric center may slightly differ from the value of the near-vision power.

The lens according to the present embodiment differs from conventional lenses mainly in the power plot of the intermediate portion. The following describes details.

Figure 4:
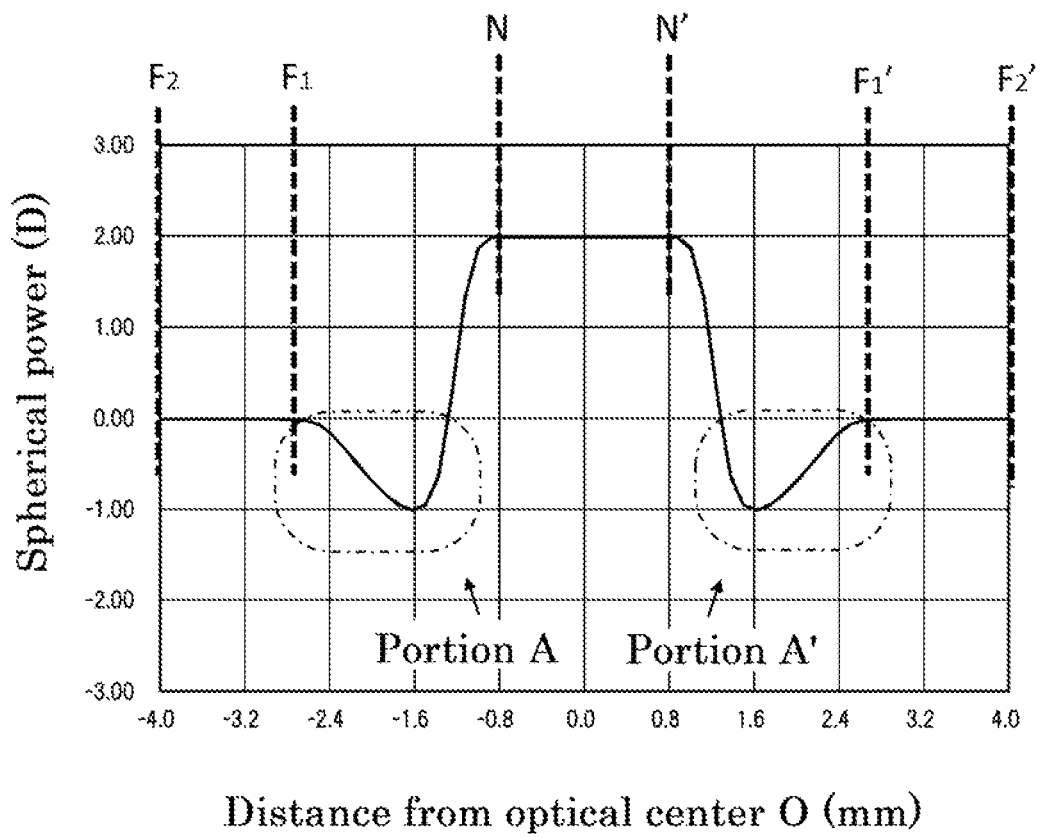
FIG. 4 is a diagram obtained by plotting the power of a multifocal contact lens (with near-vision center) according to the present embodiment from an end $F_2$ to an end $F_2'$ of an optical portion in the X-X' direction. The far-vision power S is set to 0 D, the near-vision power (S+ADD) is set to +2.00 D, and the astigmatic power C is set to 0 D. A difference between the far-vision power and each local minimum power value in portions A and A' is set to 1.00 D.

FIG. 4 is a diagram obtained by plotting the power of the multifocal contact lens (with near-vision center) according to the present embodiment from an end $F_2$ to an end $F_2'$ of the optical portion in an X-X' direction. The far-vision power S is set to 0 D, the near-vision power (S+ADD) is set to +2.00 D, and the astigmatic power C is set to 0 D. A difference between the far-vision power and each local minimum power value in portions A and A' is set to 1.00 D.

Figure 5:
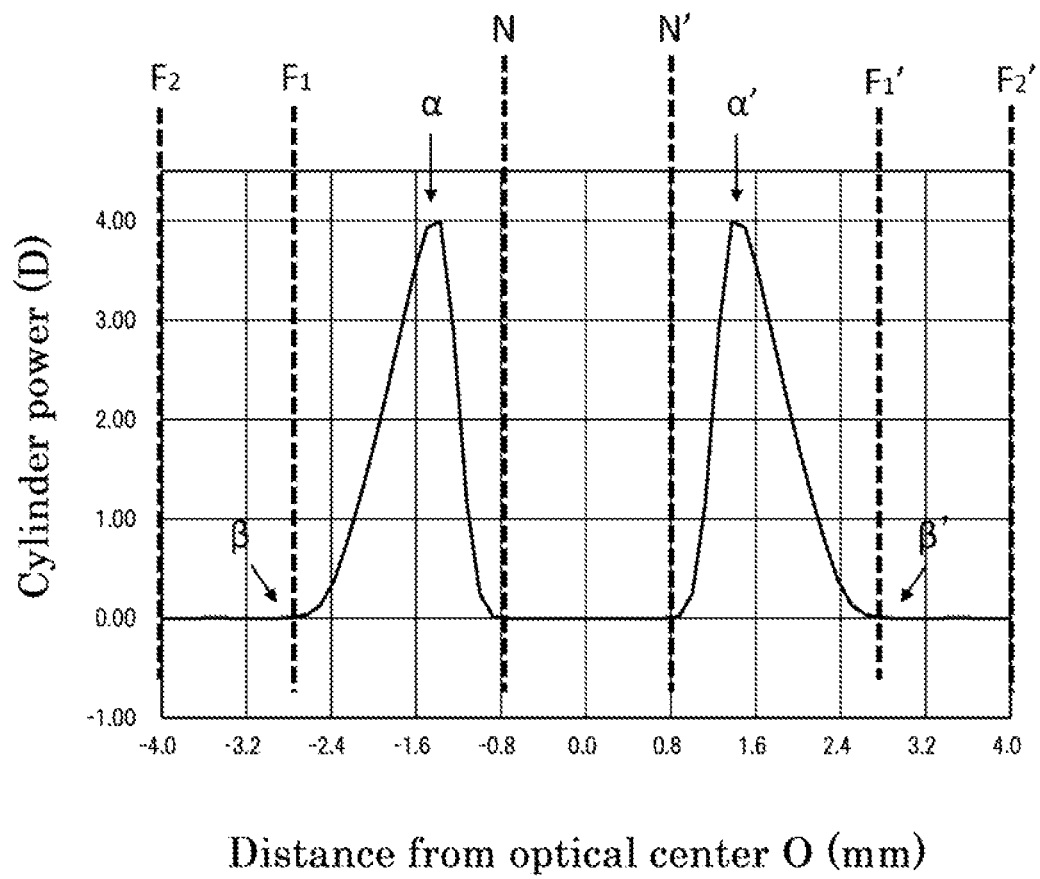
FIG. 5 is a diagram obtained by plotting the cylinder power of the lens shown in FIG. 4 from the end $F_2$ to the end $F_2'$ of the optical portion in the X-X' direction.

FIG. 5 is a diagram obtained by plotting the cylinder power of the lens shown in FIG. 4 from the end $F_2$ to the end F2' of the optical portion in the X-X' direction.

The near-vision portion in the optical portion of the lens according to the present embodiment is a portion (N-N' in FIG. 4) between a point (indicated by N in FIG. 4) at which the power lastly decreases from the near-vision power when the lens is viewed from the optical center O in an X direction (toward the outer periphery) and a point (indicated by N' in FIG. 4) at which the power lastly decreases from the near-vision power when the lens is viewed from the optical center O in an X' direction. The expression "lastly" is used in view of a case where the power is smaller than the near-vision power in a center portion of the near-vision portion.

When the lens according to the present embodiment is viewed in the X direction, the annular intermediate portion in the optical portion of the lens is a portion (N-$F_1$ in FIG. 4) from the outer edge (indicated by N in FIG. 4) of the near-vision portion to a point (indicated by $F_1$ in FIG. 4) at which the power that decreases from the outer edge of the near-vision portion to be smaller than the far-vision power and thereafter increases reaches the far-vision power. Similarly, when the lens is viewed in the X' direction, N'-$F_1'$ in FIG. 4 is the intermediate portion.

The annular far-vision portion in the optical portion of the lens according to the present embodiment is a portion other than the near-vision portion and the intermediate portion, and when the lens is viewed in the X direction and the X' direction, the far-vision portion is a portion ($F_1$-$F_2$ and $F_1'$-$F_2'$ in FIG. 4) that follows the intermediate portion in which the power increases up to the far-vision power.

As shown in FIG. 4, the intermediate portion of the lens according to the present embodiment has a shape with which the power is strengthened for far vision to be stronger than the far-vision power and thereafter weakened to reach the far-vision power when a portion A is viewed in the X direction and a portion A' is viewed in the X' direction. The portions A and A' referred to here are portions in which, after the power has decreased, the power (preferably, monotonously) decreases to be smaller than the far-vision power and thereafter again (preferably, monotonously) increases up to the far-vision power in the intermediate portion when the portion A is viewed in the X direction, for example.

More specifically, when the lens according to the present embodiment is viewed in the radial direction, a cylinder power generated in the intermediate portion immediately decreases across the intermediate portion to the far-vision portion as shown in FIG. 5. As a result, it is possible to secure a wide region in which the cylinder power is small in the far-vision portion provided along the outer edge of the intermediate portion, and vision is improved in the far-vision portion provided along the outer edge of the intermediate portion.

In the lens according to the present embodiment, it is preferable that the cylinder power (unit: diopter) satisfies the following conditions when the lens is viewed in the X direction and the X' direction.

cylinder power (indicated by an arrow β in FIG. 5) at a point at which the power reaches the far-vision power as a result of being weakened after being strengthened for far vision to be stronger than the far-vision power in the portion A≤0.30 D (preferably 0.25 D, more preferably 0.20 D, and further preferably 0.15 D)    Condition 1-1 cylinder power (indicated by an arrow β' in FIG. 5) at a point at which the power reaches the far-vision power as a result of being weakened after being strengthened for far vision to be stronger than the far-vision power in the portion A'≤0.30 D (preferably 0.25 D, more preferably 0.20 D, and further preferably 0.15 D)    Condition 2-1

If these conditions are satisfied, it is possible to reliably secure a wide region in which the cylinder power, which is an absolute value, is small in the far-vision portion provided along the outer edge of the intermediate portion.

The conditions 1-1 and 2-1 may also be replaced with the following conditions 1'-1 and 2'-1 or the following conditions 1'-1 and 2'-1 may also be added to the conditions 1-1 and 2-1.

[cylinder power (indicated by the arrow β in FIG. 5) at the point at which the power reaches the far-vision power as a result of being weakened after being strengthened for far vision to be stronger than the far-vision power in the portion A]/[maximum cylinder power (indicated by an arrow α in FIG. 5) in the intermediate portion] ≤0.30 (preferably ≤0.25, more preferably ≤0.20, and further preferably ≤0.15)    Condition 1'-1

[cylinder power (indicated by the arrow β' in FIG. 5) at the point at which the power reaches the far-vision power as a result of being weakened after being strengthened for far vision to be stronger than the far-vision power in the portion A']/[maximum cylinder power (indicated by an arrow α' in FIG. 5) in the intermediate portion] ≤0.30 (preferably ≤0.25, more preferably ≤0.20, and further preferably ≤0.15)    Condition 2'-1

If these conditions are satisfied, it can be ensured that the cylinder power generated in the intermediate portion immediately decreases when the lens is viewed from the center toward the periphery (i.e., in the X direction and the X' direction).

Note that it is preferable that the power has a local minimum value only at a point in the portion A and has a local minimum value only at a point in the portion A'. If this condition is satisfied, there is no need to provide many small recessed portions in the power plot and a lens design can be kept from becoming complex. However, this condition is not an essential condition, and a configuration is also possible in which the power has local minimum values at two or three points, for example.

Also, it is preferable that a plan view distance L between a point (outermost point) at which the power has a local minimum value in the portion A and a point (outermost point) at which the power has a local minimum value in the portion A' is 2.0 to 5.0 mm. The lower limit is more preferably 2.2 mm, and the upper limit is more preferably 4.8 mm. If this condition is satisfied, it is possible to reliably set positions from which the decreased power starts to increase to appropriate positions, and to provide the far-vision portion having a small cylinder power based on specific dimensions. However, the numerical value range described above does not necessarily have to be satisfied, and the plan view distance L may be appropriately set according to the type of the lens.

Also, it is preferable that a ratio of a difference between each local minimum power value in the portion A and the portion A' and the far-vision power to a difference between the near-vision power and the far-vision power is at least 0.15 and no greater than 1.0. The lower limit of the ratio is more preferably 0.25, further preferably 0.30, and particularly preferably 0.40, and the upper limit of the ratio is more preferably 0.90, further preferably 0.80, and particularly preferably 0.70. If this condition is satisfied, it is possible to intentionally create sufficient distortion in the intermediate portion to make the cylinder power close to 0 not only in the near-vision portion but also in the far-vision portion provided along the outer edge. However, the numerical value range described above does not necessarily have to be satisfied, and the above-described difference may be appropriately set according to conditions, and a configuration is of course possible in which the ratio of the above-described difference differs between the portion A and the portion A'.

Note that a major characteristic of the present embodiment is the behavior with which the power in the intermediate portion increases and decreases.

Therefore, there is no particular limitation on the power plot of the far-vision portion arranged along the outer edge and the power plot of the near-vision portion arranged at the center.

For example, when the lens is viewed in the X direction, the lens may also have a power plot in which the power monotonously increases or decreases, rather than becoming constant as shown in FIG. 4, after the power has changed in the intermediate portion as described above and reached the far-vision power. However, the far-vision portion is the portion having the far-vision power for seeing a predetermined distance that is farther than the near distance, and accordingly, an excessive change in the power is not preferable, and it is preferable that a change in the power in the far-vision portion is within a range of ±0.50 D (preferably ±0.25 D) with respect to the far-vision power.

Similarly, in the near-vision portion arranged at the center, the lens may also have a power plot in which the power increases or decreases from the near-vision power. However, the near-vision portion is the portion having the near-vision power for seeing the near distance, and accordingly, an excessive change in the power is not preferable, and it is preferable that a change in the power in the near-vision portion is within a range of ±0.50 D (preferably ±0.25 D) with respect to the near-vision power. Furthermore, if the power becomes smaller than the near-vision power in the near-vision portion, a sufficient power for seeing the near distance cannot be obtained, which is not preferable. Therefore, it is further preferable that a change in the power in the near-vision portion is within a range of +0.50 D (preferably +0.25 D) with respect to the near-vision power. Also, when the lens is viewed from the optical center O in the X direction and the X' direction, the near-vision portion may also have a shape with which the power is strengthened for near vision to be stronger than the near-vision power in order to sufficiently achieve the near-vision power in the near-vision portion.

The following describes variations other than the example shown in FIGS. 4 and 5 to show effectiveness of satisfying the above-described change in the strength of power and the preferable examples in the intermediate portion of the lens according to the present embodiment.

Figure 6:
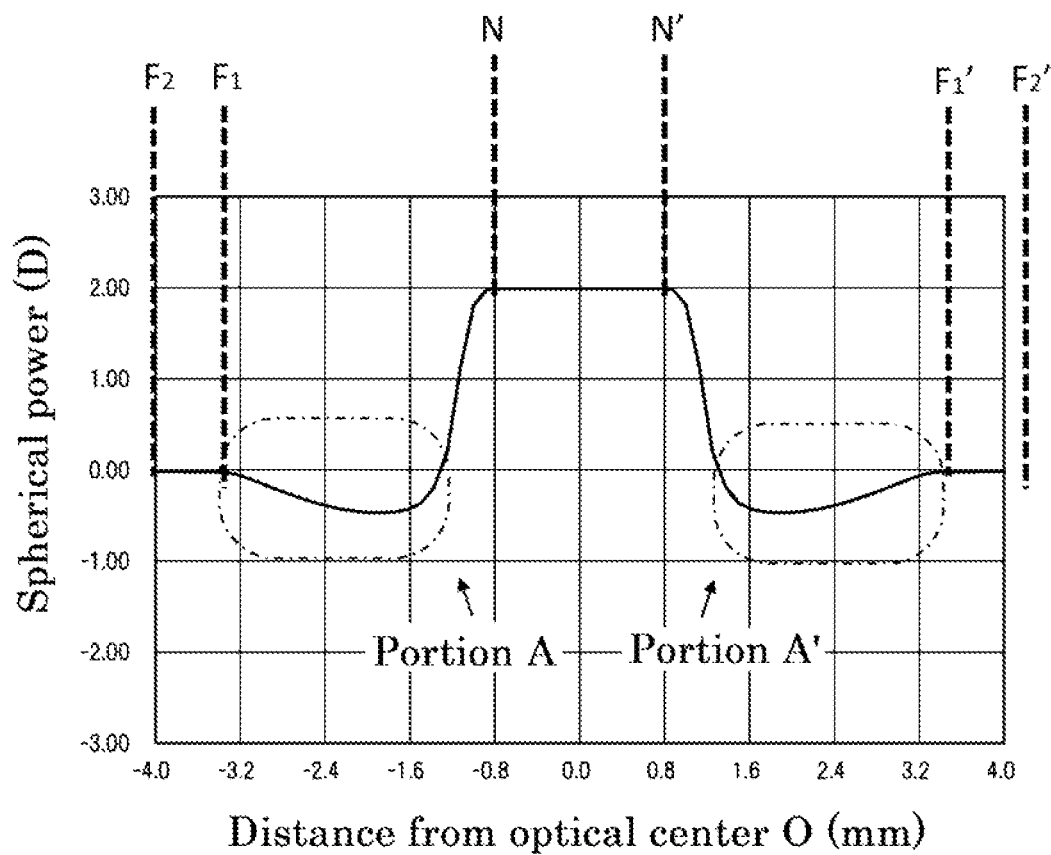
FIG. 6 is a diagram obtained by plotting the power of a multifocal contact lens (with near-vision center) according to another embodiment from an end $F_2$ to an end $F_2'$ of an optical portion in the X-X' direction. Similarly to FIG. 4, the far-vision power S is set to 0 D, the near-vision power (S+ADD) is set to +2.00 D, and the astigmatic power C is set to 0 D, but a difference between the far-vision power and each local minimum power value in portions A and A' is reduced to 0.50 D.

FIG. 6 is a diagram obtained by plotting the power of a multifocal contact lens (with near-vision center) according to another embodiment from an end $F_2$ to an end $F_2'$ of an optical portion in the X-X' direction. Similarly to FIG. 4, the far-vision power S is set to 0 D, the near-vision power (S+ADD) is set to +2.00 D, and the astigmatic power C is set to 0 D, but a difference between the far-vision power and each local minimum power value in portions A and A' is reduced to 0.50 D.

Figure 7:
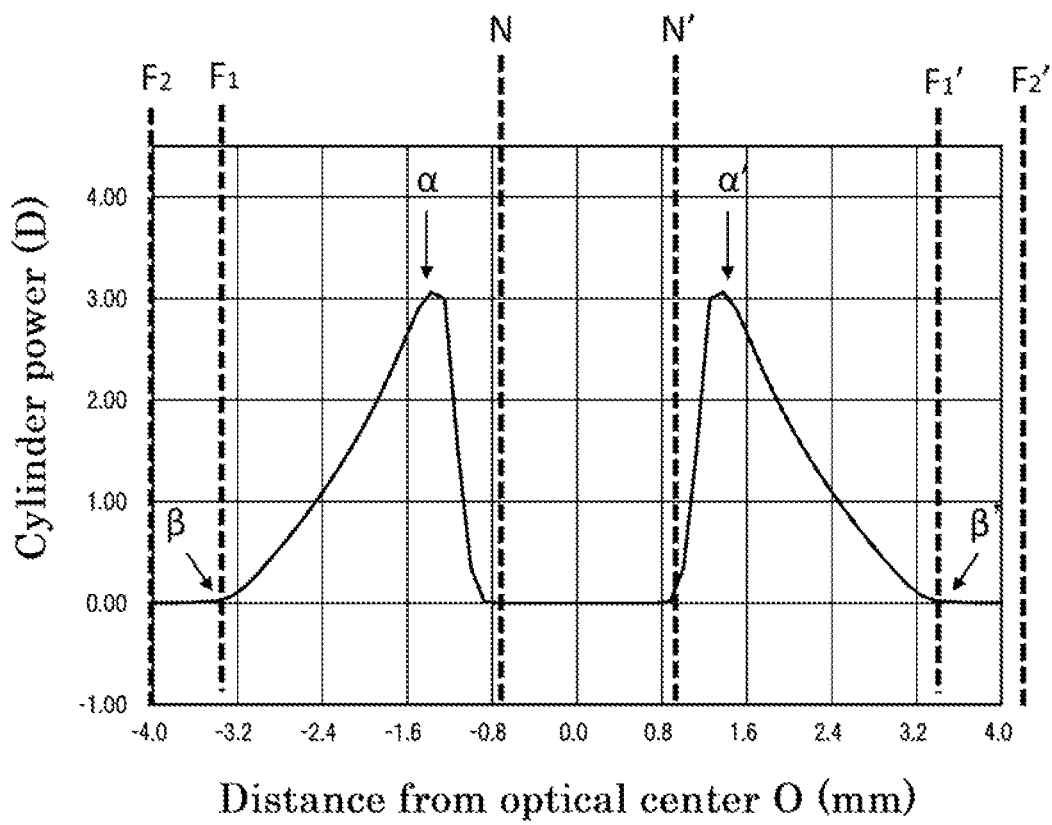
FIG. 7 is a diagram obtained by plotting the cylinder power of the lens shown in FIG. 6 from the end $F_2$ to the end $F_2'$ of the optical portion in the X-X' direction.

FIG. 7 is a diagram obtained by plotting the cylinder power of the lens shown in FIG. 6 from the end $F_2$ to the end $F_2'$ of the optical portion in the X-X' direction.

As shown in FIG. 7, the cylinder power is already close to 0 at a point (3.2 mm from the optical center O) at which the power reaches the far-vision power as a result of being weakened after being strengthened for far vision to be stronger than the far-vision power when the lens is viewed in the X direction, i.e., at the end $F_1$ of the far-vision portion, and the cylinder power is close to 0 in most of the far-vision portion ($F_1$-$F_2$).

Figure 8:
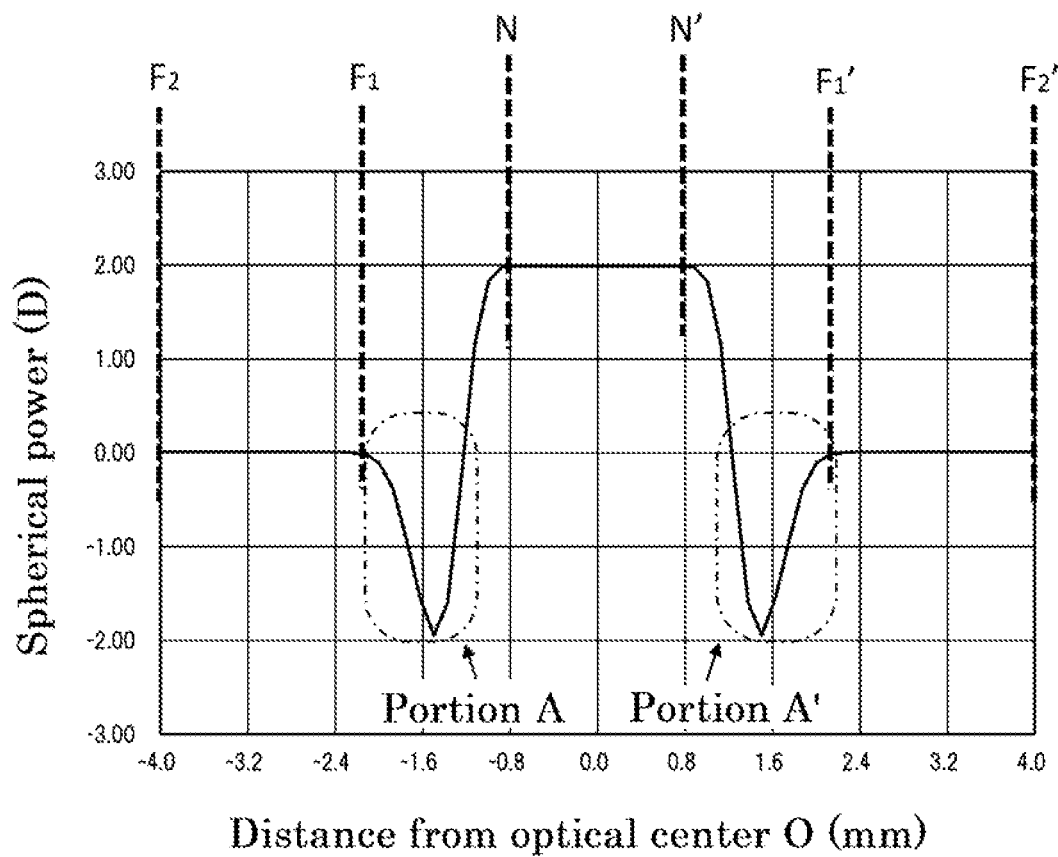
FIG. 8 is a diagram obtained by plotting the power of a multifocal contact lens (with near-vision center) according to another embodiment from an end $F_2$ to an end $F_2'$ of an optical portion in the X-X' direction. Similarly to FIG. 4, the far-vision power S is set to 0 D, the near-vision power (S+ADD) is set to +2.00 D, and the astigmatic power C is set to 0 D, but a difference between the far-vision power and each local minimum power value in portions A and A' is increased to 2.00 D.

FIG. 8 is a diagram obtained by plotting the power of a multifocal contact lens (with near-vision center) according to another embodiment from an end $F_2$ to an end $F_2'$ of an optical portion in the X-X' direction. Similarly to FIG. 4, the far-vision power S is set to 0 D, the near-vision power (S+ADD) is set to +2.00 D, and the astigmatic power C is set to 0 D, but a difference between the far-vision power and each local minimum power value in portions A and A' is increased to 2.00 D.

Figure 9:
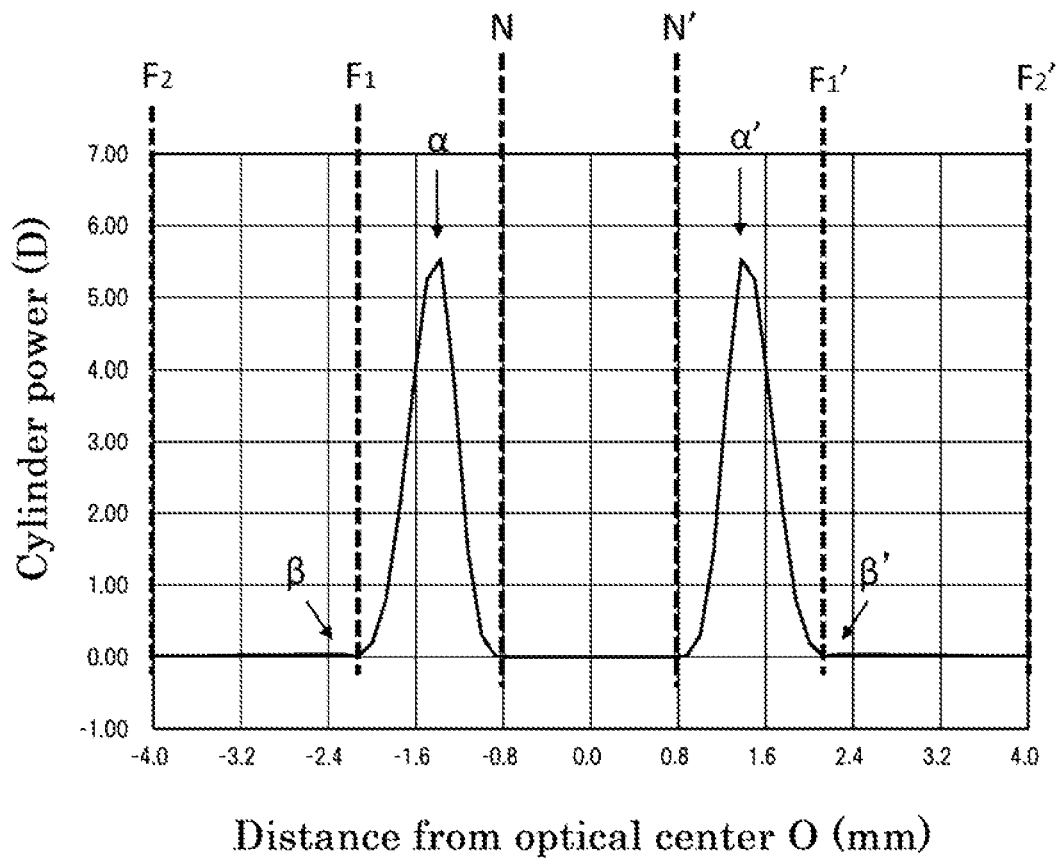
FIG. 9 is a diagram obtained by plotting the cylinder power of the lens shown in FIG. 8 from the end $F_2$ to the end $F_2'$ of the optical portion in the X-X' direction.

FIG. 9 is a diagram obtained by plotting the cylinder power of the lens shown in FIG. 8 from the end $F_2$ to the end $F_2'$ of the optical portion in the X-X' direction.

As shown in FIG. 9, the cylinder power is already no greater than 0.25 D at a point (2.6 mm from the optical center O) at which the power reaches the far-vision power as a result of being weakened after being strengthened for far vision to be stronger than the far-vision power when the lens is viewed in the X direction, i.e., at the end $F_1$ of the far-vision portion, and the cylinder power is no greater than 0.25 D in most of the far-vision portion ($F_1$-$F_2$).

Figure 2:
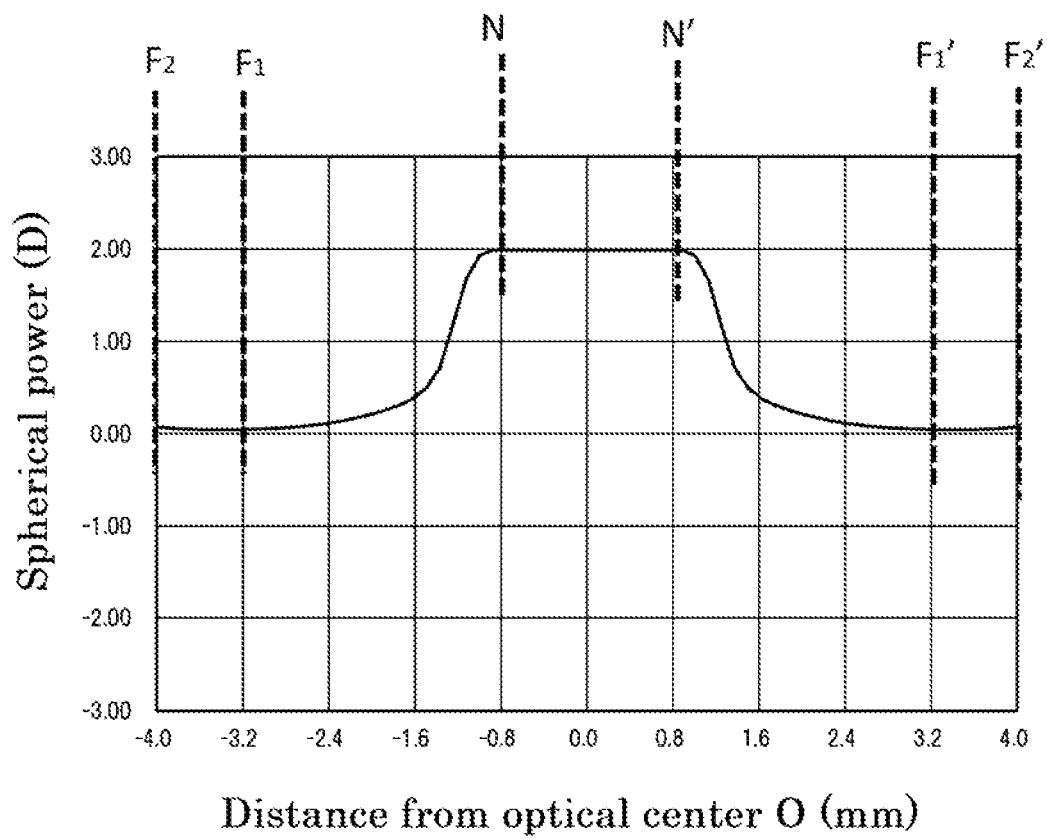
FIG. 2 is a diagram obtained by plotting the power of a conventional multifocal contact lens (with near-vision center) from an end $F_2$ to an end $F_2'$ of an optical portion in an X-X' direction. An additional power ADD of the conventional lens shown in FIG. 1 is +2.00 D. A far-vision power S is set to 0 D, a near-vision power (S+ADD) is set to +2.00 D, and an astigmatic power C is set to 0 D.
Figure 10:
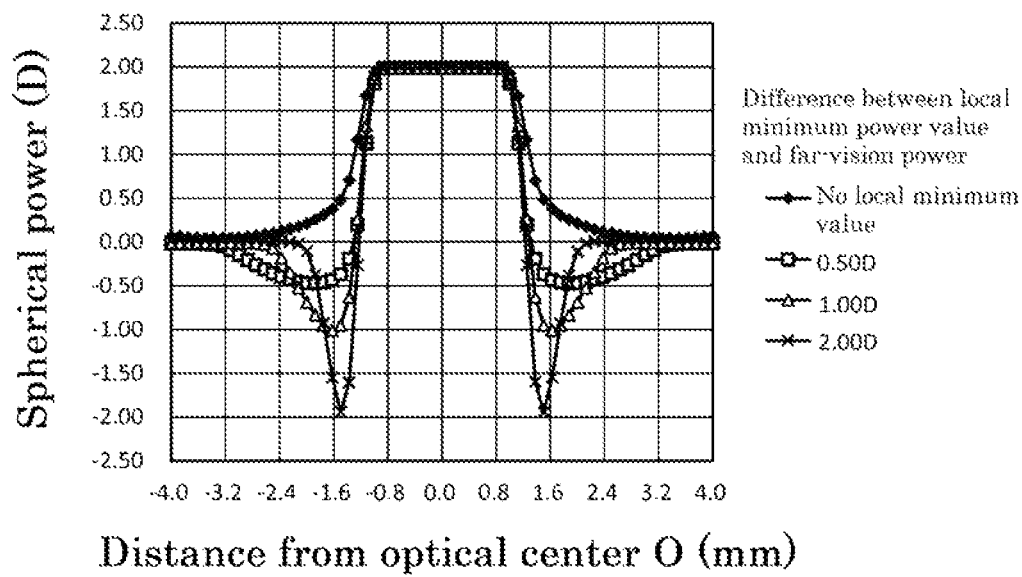
FIG. 10 is a power plot diagram collectively showing results relating to the conventional example shown in FIG. 2 and results relating to the present invention shown in FIGS. 4, 6, and 8.

FIG. 10 is a power plot diagram collectively showing results relating to the conventional example shown in FIG. 2 and results relating to the present invention shown in FIGS. 4, 6, and 8.

Figure 3:
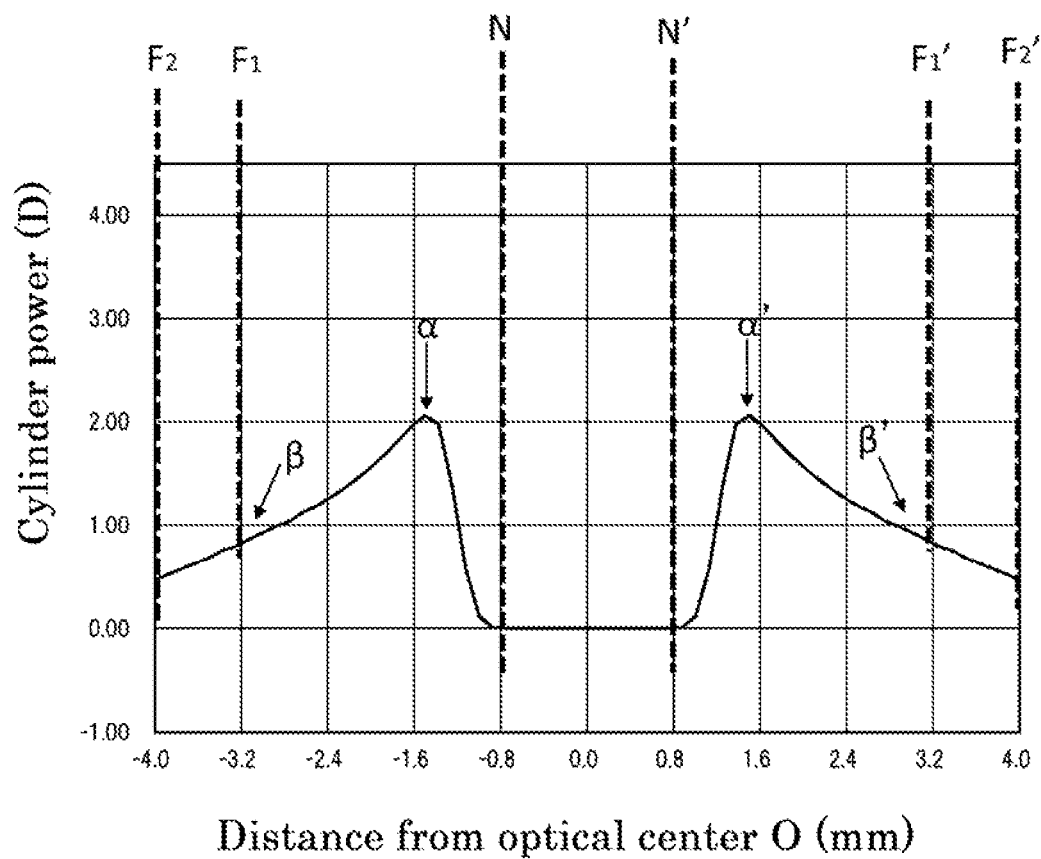
FIG. 3 is a diagram obtained by plotting the cylinder power of the lens shown in FIG. 2 from the end $F_2$ to the end $F_2'$ of the optical portion in the X-X' direction.
Figure 11:
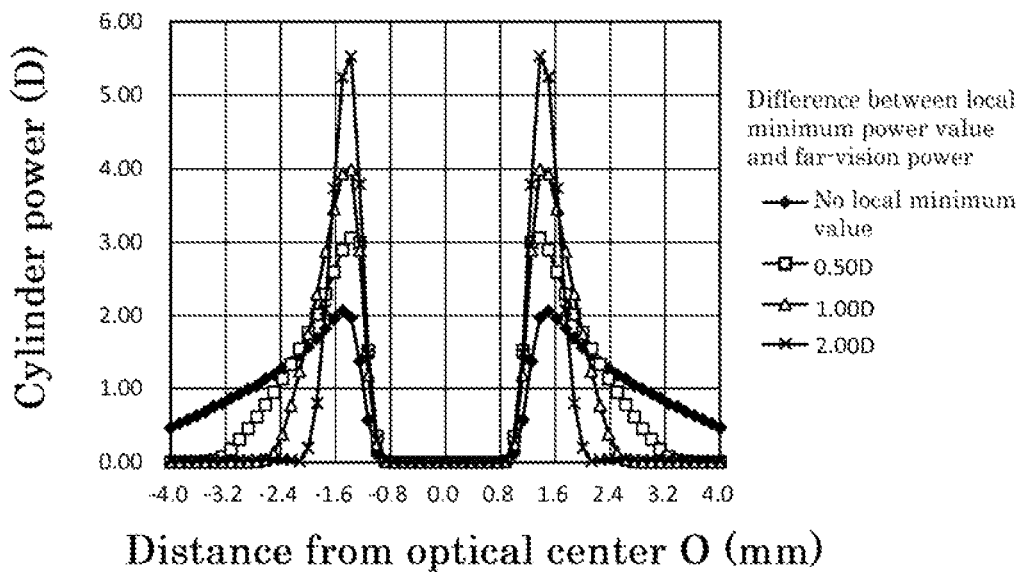
FIG. 11 is a cylinder power plot diagram collectively showing results relating to the conventional example shown in FIG. 3 and results relating to the present invention shown in FIGS. 5, 7, and 9.

FIG. 11 is a cylinder power plot diagram collectively showing results relating to the conventional example shown in FIG. 3 and results relating to the present invention shown in FIGS. 5, 7, and 9.

As shown in FIG. 11, the cylinder power can be immediately reduced in the X direction and the X' direction in the plots relating to the present invention, when compared to the plot relating to the conventional example. As a result, at points past the intermediate portion at which the power reaches the far-vision power, the cylinder power is no greater than 0.25 D in all of the plots relating to the present invention, and is close to 0 in most of the plots relating to the present invention. That is, the cylinder power generated in the intermediate portion immediately decreases and a wide region in which the cylinder power is small is secured in the far-vision portion provided along the outer edge of the intermediate portion or in the near-vision portion.

Figure 12:
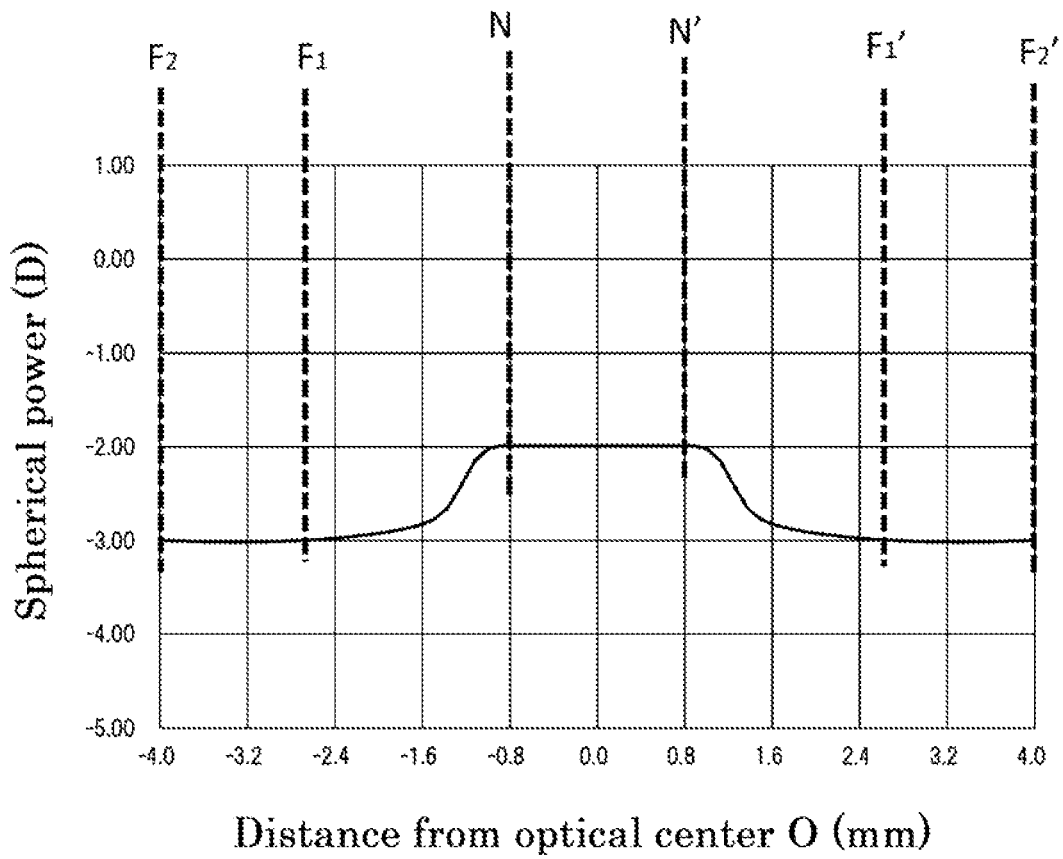
FIG. 12 is a diagram obtained by plotting the power of another conventional multifocal contact lens (with near-vision center) from an end $F_2$ to an end $F_2'$ of an optical portion in the X-X' direction. Unlike FIG. 2, the far-vision power S is set to −3.00 D, the near-vision power (S+ADD) is set to −2.00 D, and the astigmatic power C is set to 0 D.

FIG. 12 is a diagram obtained by plotting the power of another conventional multifocal contact lens (with near-vision center) from an end $F_2$ to an end $F_2'$ of an optical portion in the X-X' direction. Unlike FIG. 2, the far-vision power S is set to −3.00 D, the near-vision power (S+ADD) is set to −2.00 D, and the astigmatic power C is set to 0 D.

Figure 13:
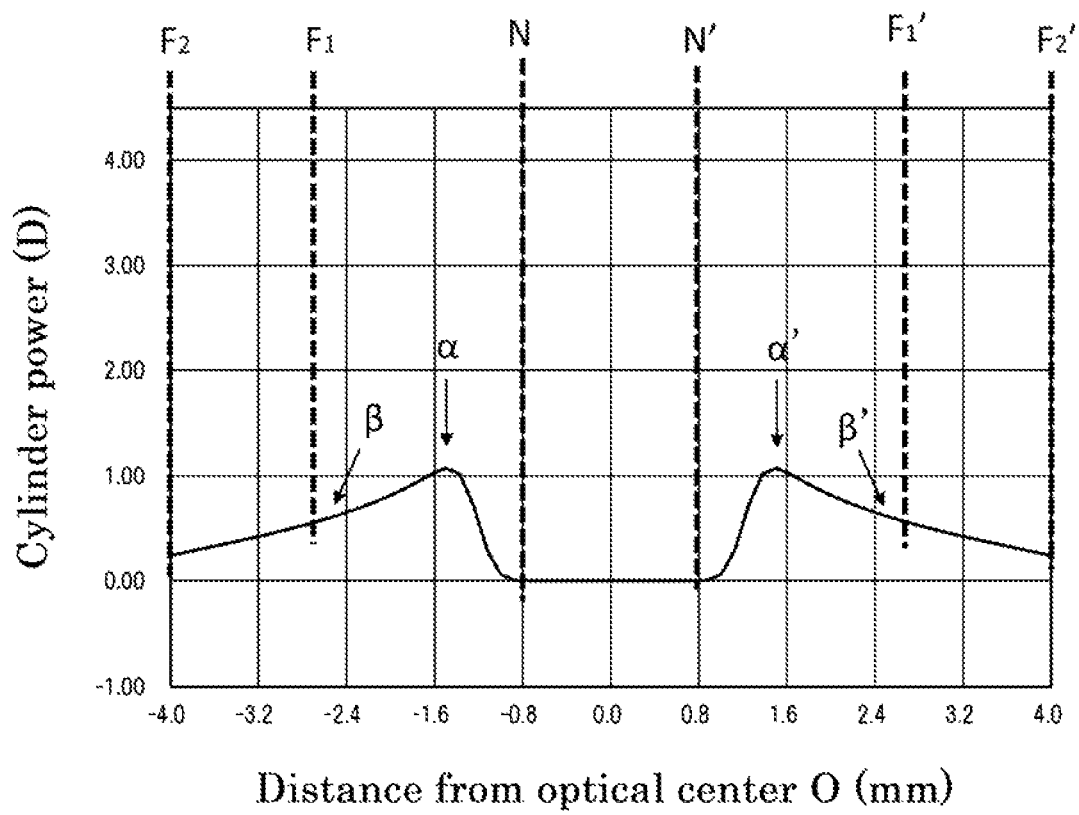
FIG. 13 is a diagram obtained by plotting the cylinder power of the lens shown in FIG. 12 from the end $F_2$ to the end $F_2'$ of the optical portion in the X-X' direction.

FIG. 13 is a diagram obtained by plotting the cylinder power of the lens shown in FIG. 12 from the end $F_2$ to the end $F_2'$ of the optical portion in the X-X' direction.

Similarly to the conventional lens (with near-vision center) shown in FIGS. 2 and 3, in the conventional lens (with near-vision center) shown in FIGS. 12 and 13, a cylinder power generated in the intermediate portion does not immediately decrease across the intermediate portion to the far-vision portion (arrow α→arrow ß and arrow α'→arrow ß' in FIG. 13).

Figure 14:
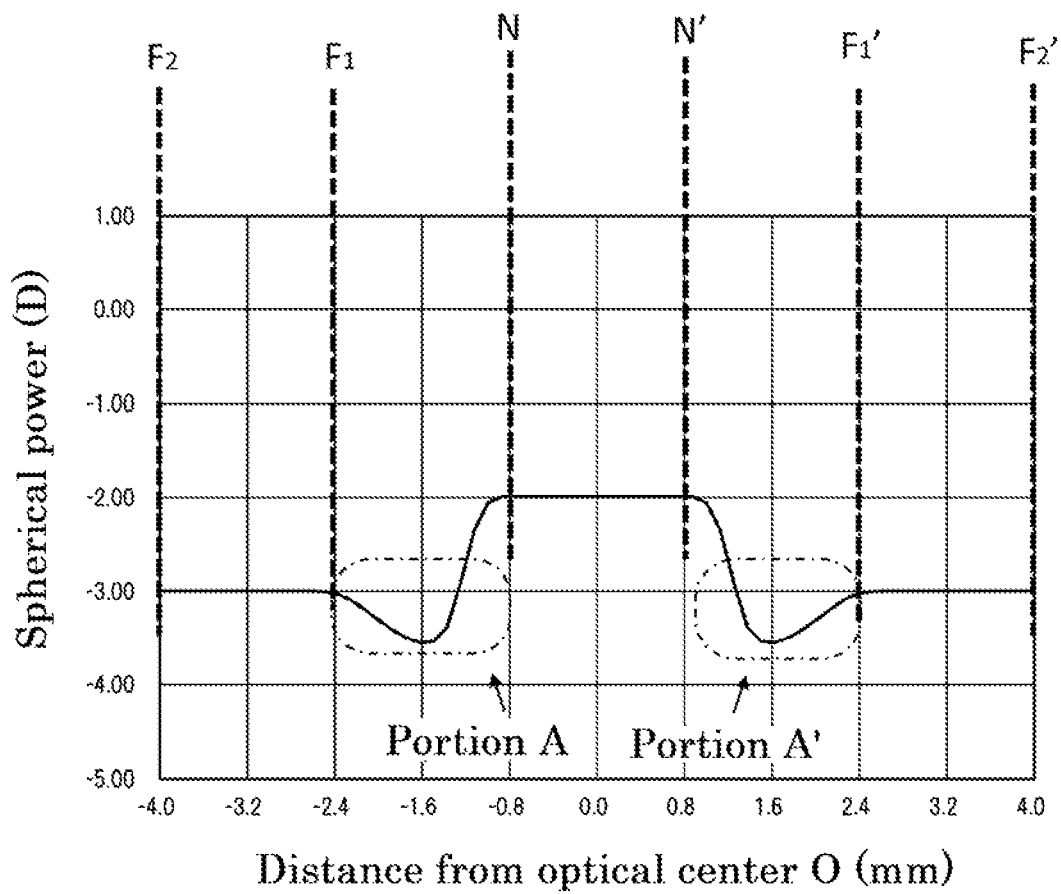
FIG. 14 is a diagram obtained by plotting the power of a multifocal contact lens (with near-vision center) according to another embodiment from an end $F_2$ to an end $F_2'$ of an optical portion in the X-X' direction. Similarly to FIG. 12, the far-vision power S is set to −3.00 D, the near-vision power (S+ADD) is set to −2.00 D, and the astigmatic power C is set to 0 D. A difference between the far-vision power and each local minimum power value in portions A and A' is set to 0.50 D.

In contrast, in a lens according to another embodiment shown in FIG. 14, which is a lens for which the far-vision power S, the near-vision power (S+ADD), and the astigmatic power C that are the same as those in the above-described other conventional lens are adopted and to which the present invention is applied, a cylinder power generated in the intermediate portion immediately decreases, and a wide region in which the cylinder power is small can be secured in the far-vision portion arranged along the outer edge of the intermediate portion or in the near-vision portion.

FIG. 14 is a diagram obtained by plotting the power of the multifocal contact lens (with near-vision center) according to the other embodiment from an end $F_2$ to and end $F_2'$ of an optical portion in the X-X' direction. Similarly to FIG. 12, the far-vision power S is set to −3.00 D, the near-vision power (S+ADD) is set to −2.00 D, and the astigmatic power C is set to 0 D. A difference between the far-vision power and each local minimum power value in portions A and A' is set to 0.50 D.

Figure 15:
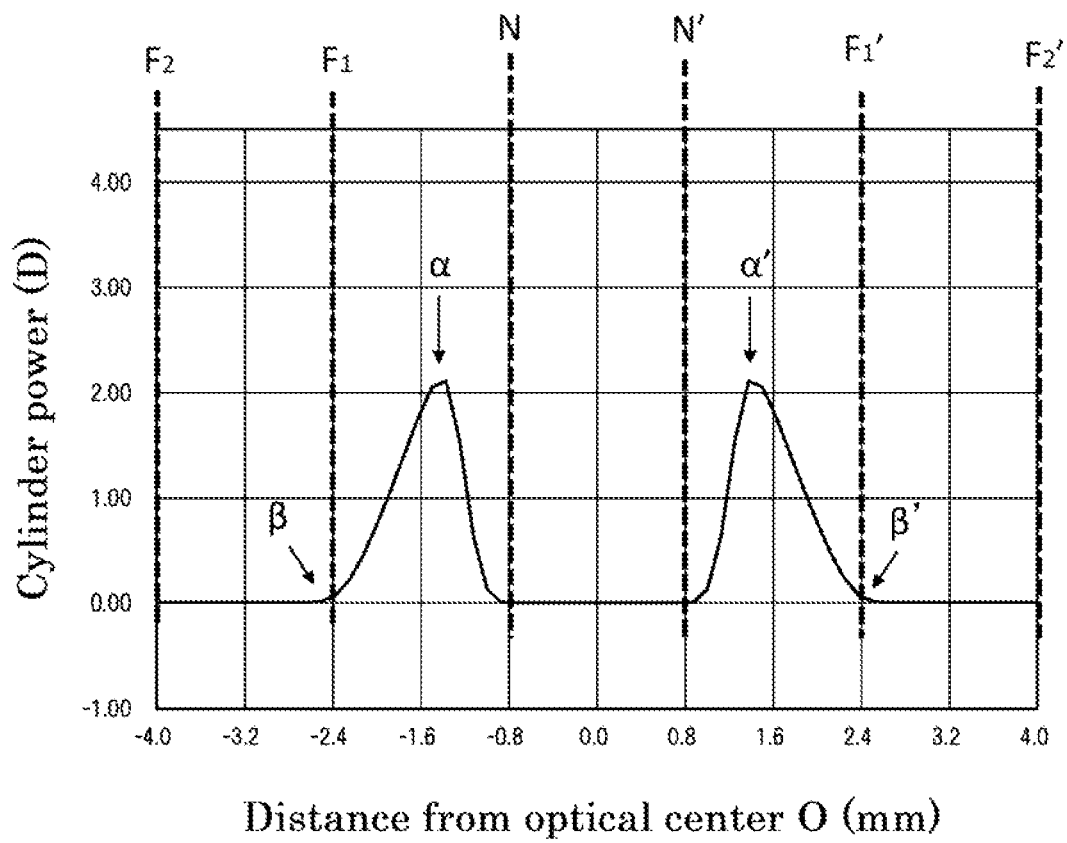
FIG. 15 is a diagram obtained by plotting the cylinder power of the lens shown in FIG. 14 from the end $F_2$ to the end $F_2'$ of the optical portion in the X-X' direction.

FIG. 15 is a diagram obtained by plotting the cylinder power of the lens shown in FIG. 14 from the end $F_2$ to the end $F_2'$ of the optical portion in the X-X' direction.

As shown in FIG. 15, the cylinder power is already close to 0 at a point (2.4 mm from the optical center O) at which the power reaches the far-vision power as a result of being weakened after being strengthened for far vision to be stronger than the far-vision power when the lens is viewed in the X direction, i.e., at the end $F_1$ of the far-vision portion, and the cylinder power is close to 0 in most of the far-vision portion ($F_1$-$F_2$).

Note that the present invention does not exclude a case (a trifocal lens or the like) in which an annular near-vision portion or a second far-vision portion for seeing a farther distance when compared to the above-described far-vision portion is further provided in the periphery of the far-vision portion in addition to the near-vision portion provided at the center and the far-vision portion provided in the periphery of the near-vision portion with the intermediate portion interposed between the near-vision portion and the far-vision portion. In this example, if the annular far-vision portion and the annular second far-vision portion, which is provided in the periphery with an annular second intermediate portion that differs from the above-described intermediate portion interposed between the annular far-vision portion and the annular second far-vision portion, have the characteristics of the present embodiment, the "near-vision portion arranged close to the center" in the above-described characteristics corresponds to the "annular far-vision portion", and the "annular far-vision portion" in the above-described characteristics corresponds to the "annular second far-vision portion".

That is, the "near-vision portion arranged close to the center" referred to in the present specification includes a near-vision portion that is arranged at the center so as to include the optical center O and a near-vision portion that does not include the optical center O but is arranged close to the center and has a ring shape.

Note that the intermediate portion in the present embodiment is defined using the power plot in the above description, but it is also possible to define the intermediate portion using the shape (curvature) of the front surface instead of the power plot. This is because a surface (rear surface) of a conventional lens that comes into contact with a cornea needs to have a shape corresponding to a surface (e.g., a spherical surface or a toric surface) that conforms to the shape of the cornea. Accordingly, the power needs to be adjusted by adjusting the shape of a surface (front surface) on the eyelid side. Actually, each power plot referred to in the present specification is obtained by adjusting the shape of the front surface while forming the rear surface as a spherical surface.

Therefore, the characteristics of the power plot can also be expressed using the shape (curvature) of the front surface of the lens as follows.

An ophthalmic lens including an optical portion that includes a near-vision portion having a near-vision power for seeing a near distance, a far-vision portion having a far-vision power for seeing a distance that is farther than the near distance, and an annular intermediate portion that connects the near-vision portion and the far-vision portion to each other, the near-vision portion or the far-vision portion being arranged at the center, the near-vision portion or the far-vision portion that is not arranged at the center being arranged in a ring shape along an outer edge of the intermediate portion, wherein the intermediate portion includes a portion A in which a curvature is reduced and thereafter increased when the lens is viewed in an X direction from the center toward the periphery, and the intermediate portion includes a portion A' in which the curvature is reduced and thereafter increased when the lens is viewed in an X' direction from the center toward the periphery, the X' direction being exactly opposite to the X direction.

Preferably, the curvature has a local minimum value only at a point in the portion A and has a local minimum value only at a point in the portion A'.

Preferably, a plan view distance between a point at which the curvature has a local minimum value in the portion A and a point at which the curvature has a local minimum value in the portion A' is 1.6 to 3.8 mm.

Note that it is also possible to apply preferable examples of the case where the power is used to define the intermediate portion to a case where the radius of curvature is used, by converting the power to the radius of curvature as appropriate.

Note that, in the lens according to the present embodiment, it is possible to make the cylinder power low in a wide area of the far-vision portion owing to the configurations described above. Specifically, when a straight line X-X' is rotated relative to the lens about the optical center O from 0° to 180°, a portion of the far-vision portion in which the cylinder power is no greater than 0.50 D is preferably at least 80 area %, more preferably at least 90 area %, and further preferably at least 95 area %.

Note that, in the present specification, "area %" means a percentage of a total area of portions (e.g., two fan-shaped portions (a portion A between 0° and 180° and a portion A' between 180° and 360°) that are surrounded by the optical center O and arcs defining the outermost edge of the optical portion) that have the above-described shape with respect to an area of the optical portion in a plan view when the straight line X-X' is rotated in the plan view relative to the lens about the optical center O from 0° to 180° with respect to the optical center.

Incidentally, there is no boundary that can be visually recognized between the optical portion and the peripheral portion of the lens as described above, but the optical portion and the peripheral portion can be distinguished using a device (power meter) for measuring the power of the lens.

1-1-2. Far-Vision Portion Arranged at the Center and Near-Vision Portion Arranged in Ring Shape Along Outer Edge of Center Portion The idea of the present invention can also be applied to a case where the near-vision portion is arranged at the center, the annular intermediate portion is arranged along the outer edge of the near-vision portion, and the far-vision portion is arranged in a ring shape along the outer edge of the intermediate portion, contrary to the above-described example. Note that the positions of the near-vision portion and the far-vision portion shown in FIG. 4 and the like described above are interchanged in a plan view configuration.

In this example, the far-vision portion is arranged at the center and the near-vision portion is arranged in a ring shape along an outer edge of a center portion. Accordingly, the power at the optical center O is set to be lower than the power in the near-vision portion. Note that values of the far-vision power S and the additional power ADD (and the astigmatic power C in cases where astigmatism is corrected) are usually given as a prescription of a lens. Note that a configuration is also possible in which the lens has the value of the far-vision power exactly at the position of the optical center O (i.e., power at the optical center O=far-vision power S), and if the optical center O is shifted from the geometric center, the power at the geometric center may slightly differ from the value of the far-vision power.

Figure 16:
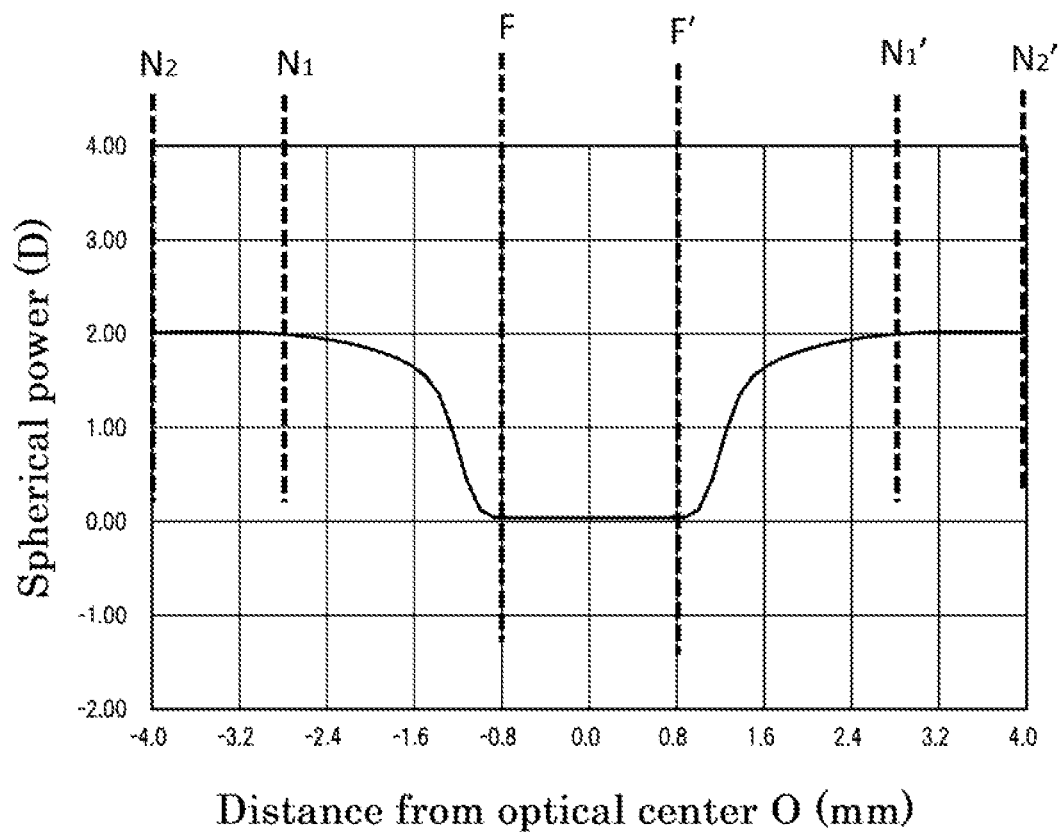
FIG. 16 is a diagram obtained by plotting the power of another conventional multifocal contact lens (with far-vision center) from an end $N_2$ to an end $N_2'$ of an optical portion in the X-X' direction. The additional power ADD of the conventional lens shown in FIG. 16 is +2.00 D. The far-vision power S is set to 0 D, the near-vision power (S+ADD) is set to +2.00 D, and the astigmatic power C is set to 0 D.

FIG. 16 is a diagram obtained by plotting the power of another conventional multifocal contact lens (with far-vision center) from an end $N_2$ to an end $N_2'$ of an optical portion in the X-X' direction. The additional power ADD of the conventional lens shown in FIG. 16 is +2.00 D. The far-vision power S is set to 0 D, the near-vision power (S+ADD) is set to +2.00 D, and the astigmatic power C is set to 0 D.

Figure 17:
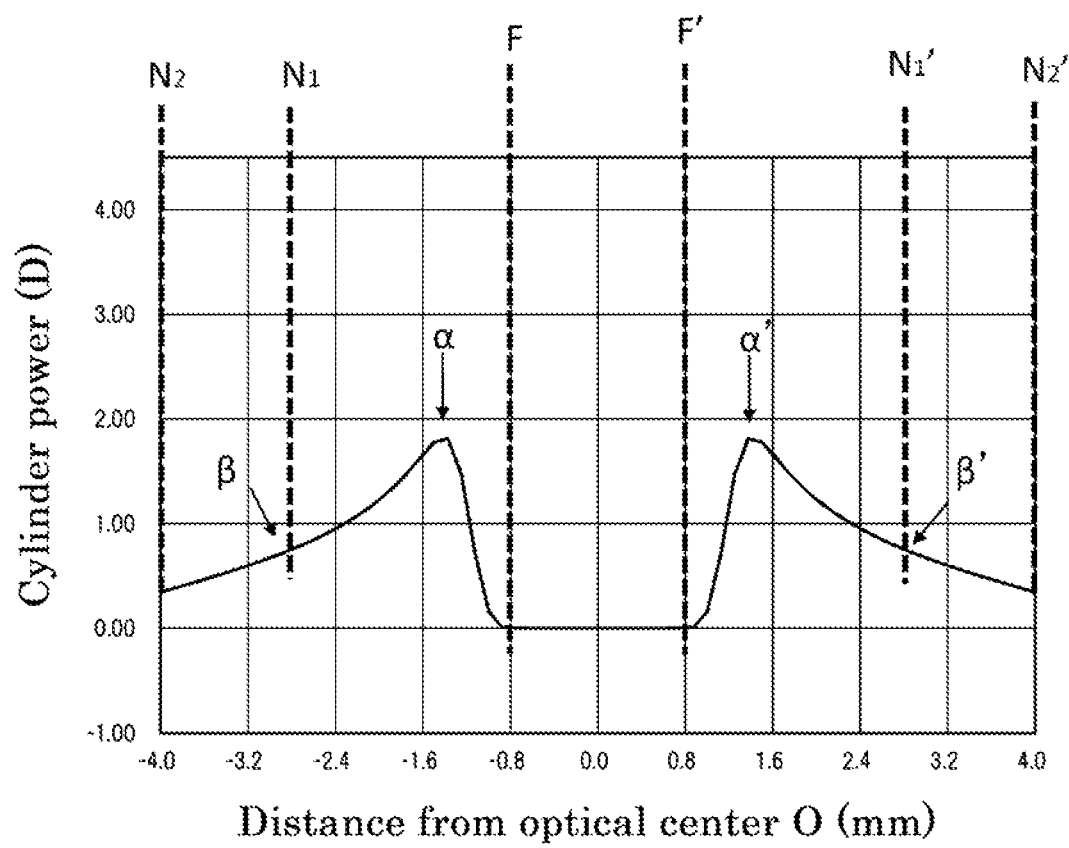
FIG. 17 is a diagram obtained by plotting the cylinder power of the lens shown in FIG. 16 from the end $N_2$ to the end $N_2'$ of the optical portion in the X-X' direction.

FIG. 17 is a diagram obtained by plotting the cylinder power of the lens shown in FIG. 16 from the end $N_2$ to the end $N_2'$ of the optical portion in the X-X' direction.

Similarly to the conventional lens (with near-vision center) shown in FIGS. 2 and 3, in the conventional lens (with far-vision center) shown in FIGS. 16 and 17, a cylinder power generated in the intermediate portion does not immediately decrease across the intermediate portion to the near-vision portion (arrow α→arrow ß and arrow α'→arrow ß' in FIG. 17).

Figure 18:
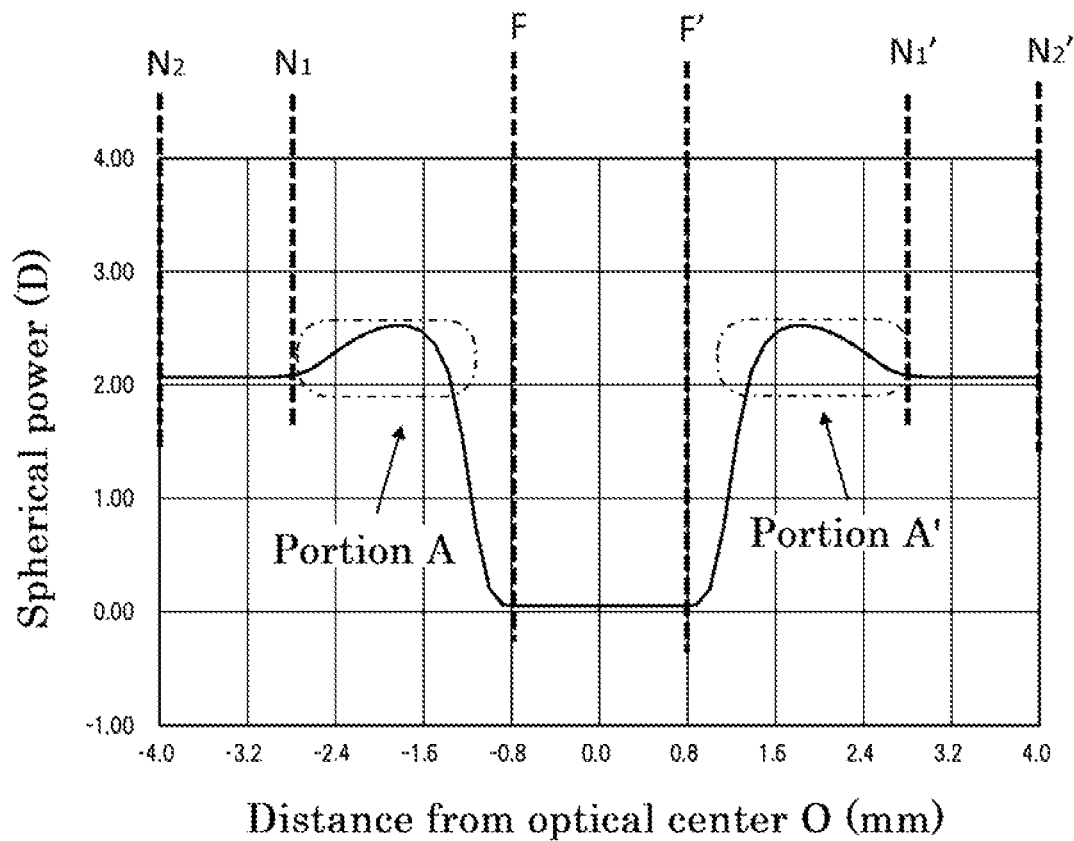
FIG. 18 is a diagram obtained by plotting the power of a multifocal contact lens (with far-vision center) according to the present example from an end $N_2$ to an end $N_2'$ of an optical portion in the X-X' direction. The far-vision power S is set to 0 D, the near-vision power (S+ADD) is set to +2.00 D, and the astigmatic power C is set to 0 D. A difference between the near-vision power and each local maximum power value in portions A and A' is set to 0.50 D.

A lens according to this example shown in FIG. 18 differs from the conventional lens mainly in the power plot of the intermediate portion. The following describes details FIG. 18 is a diagram obtained by plotting the power of a multifocal contact lens (with far-vision center) according to this example from an end $N_2$ to an end $N_2'$ of an optical portion in the X-X' direction. The far-vision power S is set to 0 D, the near-vision power (S+ADD) is set to +2.00 D, and the astigmatic power C is set to 0 D. A difference between the near-vision power and each local maximum power value in portions A and A' is set to 0.50 D.

Figure 19:
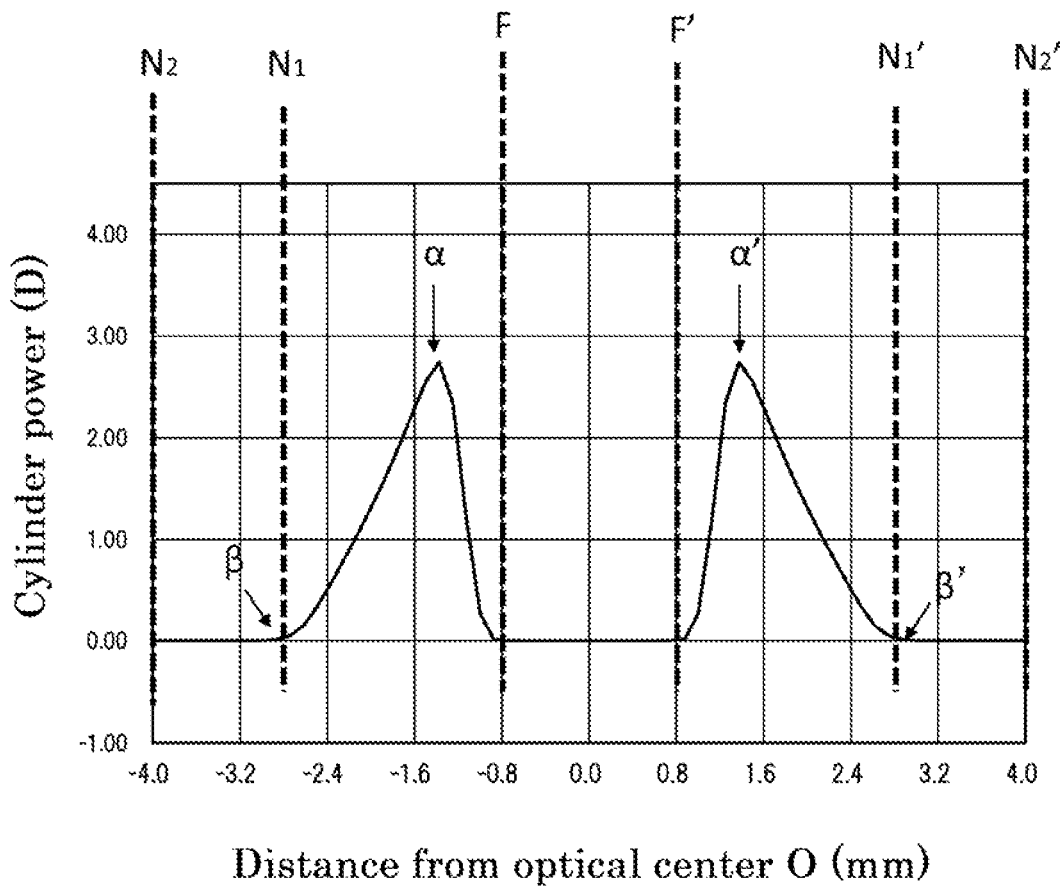
FIG. 19 is a diagram obtained by plotting the cylinder power of the lens shown in FIG. 18 from the end $N_2$ to the end $N_2'$ of the optical portion in the X-X' direction.

FIG. 19 is a diagram obtained by plotting the cylinder power of the lens shown in FIG. 18 from the end $N_2$ to the end $N_2'$ of the optical portion in the X-X' direction.

The far-vision portion in the optical portion of the lens according to this example is a portion (F-F' in FIG. 4) between a point (indicated by F in FIG. 18) at which the power lastly increases from the far-vision power when the lens is viewed from the optical center O in the X direction (toward the outer periphery) and a point (indicated by F' in FIG. 18) at which the power lastly increases from the far-vision power when the lens is viewed from the optical center O in the X' direction. The expression "lastly" is used in view of a case where the power is smaller than the far-vision power in a center portion of the far-vision portion.

When the lens according to this example is viewed in the X direction, the annular intermediate portion in the optical portion of the lens is a portion (F-$N_1$ in FIG. 18) from the outer edge (indicated by F in FIG. 18) of the far-vision portion to a point (indicated by $N_1$ in FIG. 18) at which the power that increases from the outer edge of the far-vision portion to be larger than the near-vision power and thereafter decreases reaches the near-vision power. Similarly, when the lens is viewed in the X' direction, F'-$N_1$' in FIG. 4 is the intermediate portion.

The annular near-vision portion in the optical portion of the lens according to this example is a portion other than the far-vision portion and the intermediate portion, and when the lens is viewed in the X direction and the X' direction, the near-vision portion is a portion ($N_1$-$N_2$ and $N_1$'-$N_2$' in FIG. 4) that follows the intermediate portion in which the power decreases to the near-vision power.

The intermediate portion of the lens according to this example has a shape with which the power is strengthened for near vision to be stronger than the near-vision power and thereafter weakened to reach the near-vision power when a portion A is viewed in the X direction and a portion A' is viewed in the X' direction. The portions A and A' referred to here are portions in which, after the power has increased, the power (preferably, monotonously) increases to be larger than the near-vision power and thereafter again (preferably, monotonously) decreases to reach the near-vision power in the intermediate portion when the portion A is viewed in the X direction, for example.

More specifically, when the lens according to the present embodiment is viewed in the radial direction, a cylinder power generated in the intermediate portion immediately decreases across the intermediate portion to the near-vision portion as shown in FIG. 19. As a result, it is possible to secure a wide region in which the cylinder power is small in the near-vision portion provided along the outer edge of the intermediate portion, and vision is improved in the near-vision portion provided along the outer edge of the intermediate portion.

In the lens according to the present embodiment, it is preferable that the cylinder power (unit: diopter) satisfies the following conditions when the lens is viewed in the X direction and the X' direction.

cylinder power (indicated by an arrow ß in FIG. 19) at a point at which the power reaches the near-vision power as a result of being weakened after being strengthened for near vision to be stronger than the near-vision power in the portion $A$≤0.30 D (preferably ≤0.25 D, more preferably ≤0.20 D, and further preferably ≤0.15 D), and    Condition 1-2

[cylinder power (indicated by an arrow ß' in FIG. 19) at a point at which the power reaches the near-vision power as a result of being weakened after being strengthened for near vision to be stronger than the near-vision power in the portion $A'$]/[maximum cylinder power (indicated by an arrow α' in FIG. 19) in the intermediate portion]≤0.30 D (preferably ≤0.25 D, more preferably ≤0.20 D, and further preferably ≤0.15 D).    Condition 2-2

If these conditions are satisfied, it is possible to reliably secure a wide region in which the cylinder power, which is an absolute value, is small in the near-vision portion provided along the outer edge of the intermediate portion.

The conditions 1-2 and 2-2 may also be replaced with the following conditions 1'-2 and 2'-2 or the following conditions 1'-2 and 2'-2 may also be added to the conditions 1-2 and 2-2.

[cylinder power (indicated by the arrow ß in FIG. 5) at the point at which the power reaches the near-vision power as a result of being weakened after being strengthened for near vision to be stronger than the near-vision power in the portion $A$]/[maximum cylinder power (indicated by an arrow α in FIG. 5) in the intermediate portion]≤0.30 (preferably ≤0.25, more preferably ≤0.20, and further preferably ≤0.15)    Condition 1'-2

[cylinder power (indicated by the arrow ß' in FIG. 5) at the point at which the power reaches the near-vision power as a result of being weakened after being strengthened for near vision to be stronger than the near-vision power in the portion $A'$]/[maximum cylinder power (indicated by an arrow α' in FIG. 5) in the intermediate portion]≤0.30 (preferably ≤0.25, more preferably ≤0.20, and further preferably ≤0.15)    Condition 2'-2

If these conditions are satisfied, it can be ensured that the cylinder power generated in the intermediate portion immediately decreases when the lens is viewed from the center toward the periphery (i.e., in the X direction and the X' direction).

Note that it is preferable that the power has a local maximum value only at a point in the portion A and has a local maximum value only at a point in the portion A'. If this condition is satisfied, there is no need to provide many small protruding portions in the power plot and a lens design can be kept from becoming complex. However, this condition is not an essential condition, and a configuration is also possible in which the power has local maximum values at two or three points, for example.

Also, it is preferable that a plan view distance L between a point (outermost point) at which the power has a local maximum value in the portion A and a point (outermost point) at which the power has a local maximum value in the portion A' is 2.0 to 5.0 mm. The lower limit is more preferably 2.2 mm, and the upper limit is more preferably 4.8 mm. If this condition is satisfied, it is possible to reliably set positions from which the increased power starts to decrease to appropriate positions, and to provide the near-vision portion having a small cylinder power based on specific dimensions. However, the numerical value range described above does not necessarily have to be satisfied, and the plan view distance L may be appropriately set according to the type of the lens.

Also, it is preferable that a ratio of a difference between each local maximum power value in the portion A and the portion A' and the near-vision power to a difference between the near-vision power and the far-vision power is at least 0.15 and no greater than 1.0. The lower limit of the ratio is more preferably 0.25, further preferably 0.30, and particularly preferably 0.40, and the upper limit of the ratio is more preferably 0.90, further preferably 0.80, and particularly preferably 0.70. If this condition is satisfied, it is possible to intentionally create sufficient distortion in the intermediate portion to make the cylinder power close to 0 not only in the far-vision portion but also in the near-vision portion provided along the outer edge. However, the numerical value range described above does not necessarily have to be satisfied, and the above-described difference may be appropriately set according to conditions, and a configuration is of course possible in which the ratio of the above-described difference differs between the portion A and the portion A'.

Note that a major characteristic of the present embodiment is the behavior with which the power in the intermediate portion increases and decreases. Therefore, there is no particular limitation on the power plot of the near-vision portion arranged along the outer edge and the power plot of the far-vision portion arranged at the center.

For example, when the lens is viewed in the X direction, the lens may also have a power plot in which the power continuously increases or decreases, rather than becoming constant as shown in FIG. 18, after the power has changed in the intermediate portion as described above and reached the near-vision power. However, the near-vision portion is the portion having the near-vision power for seeing the near distance, and accordingly, an excessive change in the power is not preferable, and it is preferable that a change in the power in the near-vision portion is within a range of ±0.50 D (preferably ±0.25 D) with respect to the near-vision power.

Similarly, in the far-vision portion arranged at the center, the lens may also have a power plot in which the power increases or decreases from the far-vision power. However, the far-vision portion is the portion having the far-vision power for seeing a predetermined distance that is farther than the near distance, and accordingly, an excessive change in the power is not preferable, and it is preferable that a change in the power in the far-vision portion is within a range of ±0.50 D (preferably ±0.25 D) with respect to the near-vision power. Furthermore, if the power becomes larger than the far-vision power in the far-vision portion, the power becomes unsuitable for seeing the far distance, which is not preferable. Therefore, it is further preferable that a change in the power in the far-vision portion is within a range of −0.50 D (preferably −0.25 D) with respect to the far-vision power. Also, when the lens is viewed from the optical center O in the X direction and the X' direction, the far-vision portion may also have a shape with which the power is strengthened for far vision to be stronger than the far-vision power in order to sufficiently achieve the far-vision power in the far-vision portion.

Note that the present invention does not exclude a case in which the far-vision portion is provided at the center, the near-vision portion is provided in the periphery of the far-vision portion with the intermediate portion interposed between the far-vision portion and the near-vision portion, and an annular far-vision portion or a second near-vision portion for seeing a nearer distance when compared to the above-described near-vision portion is further provided in the periphery of the near-vision portion. In this example, if the annular near-vision portion and the annular second near-vision portion, which is provided in the periphery with an annular second intermediate portion that differs from the above-described intermediate portion being interposed between the annular near-vision portion and the annular second near-vision portion, have the characteristics of the present embodiment, the "far-vision portion arranged close to the center" in the above-described characteristics corresponds to the "annular near-vision portion", and the "annular near-vision portion" in the above-described characteristics corresponds to the "annular second near-vision portion".

That is, the "far-vision portion arranged close to the center" referred to in the present specification includes a far-vision portion that is arranged at the center so as to include the optical center O and a far-vision portion that does not include the optical center O but is arranged close to the center and has a ring shape.

Note that, in the lens according to the present embodiment, it is possible to make the cylinder power low in a wide area of the near-vision portion owing to the configurations described above. Specifically, when the straight line X-X' is rotated relative to the lens about the optical center O from 0° to 180°, a portion of the near-vision portion in which the cylinder power is no greater than 0.50 D is preferably at least 80 area %, more preferably at least 90 area %, and further preferably at least 95 area %.

In a case where the far-vision portion is defined using the shape (curvature) of the front surface instead of the power plot, the principle is similar to that of the above-described case where the near-vision portion is arranged at the center, and the definition can be made by replacing the near-vision portion with the far-vision portion, replacing "local minimum" with "local maximum", and replacing "(the curvature being) reduced and thereafter increased" with "(the curvature being) increased and thereafter reduced".

1-2. Other Contact Lenses

Although multifocal contact lenses are described as examples in the present embodiments, the technical idea of the present invention can also be applied to other contact lenses.

For example, in multifocal toric contact lenses as well, the above-described behavior of power is not hindered due to the toric shape. This is because a uniform difference in curvature (difference between the curvature in the radial direction and the curvature in the circumferential direction) is provided in a surface of a toric contact lens, and there is no problem in making the curvature in the circumferential direction closer to the curvature in the radial direction in the intermediate portion as described as the findings of the present invention. Therefore, the technical idea of the present invention can also be applied to toric contact lenses.

Note that the lens according to the present embodiment including the portions A and A' described above may be a soft contact lens or a hard contact lens, but a soft contact lens, which hardly moves when arranged on a cornea, is more preferable in terms of providing sufficient optical performance and getting customer satisfaction from wearers.

It is also possible to impart a nearsightedness progression suppressing effect to the lens according to the present embodiment. Such a lens will be referred to as a "nearsightedness progression suppressing lens". The nearsightedness progression suppressing effect is achieved by causing light that enters an eyeball to converge in front of a retina (on an object side as viewed from the retina).

This nearsightedness progression suppressing effect can be realized with a lens with far-vision center, for example. Specifically, a configuration is also possible in which a far-vision portion arranged at the center has a shape that reflects prescription values, and a near-vision portion that has a higher power than the far-vision portion (causing light to converge in front of the retina) is provided along an outer edge of an intermediate portion that is interposed between the far-vision portion and the near-vision portion.

The nearsightedness progression suppressing effect can also be realized with a lens with near-vision center. Specifically, a configuration is also possible in which a near-vision portion arranged at the center causes light to converge in front of the retina, and a far-vision portion that has a lower power than the near-vision portion, i.e., has a shape that reflects prescription values is provided along an outer edge of an intermediate portion that is interposed between the near-vision portion and the far-vision portion.

That is, in the case of a lens imparted with the nearsightedness progression suppressing effect, the effects of the present invention can be achieved if any of the regions that are concentrically arranged in the lens has a shape that reflects prescription values for a wearer. The far-vision portion and the near-vision portion (particularly, the near-vision portion) that are arranged close to the center or close to the outer edge relative to the annular intermediate portion having the characteristics of the present embodiment do not necessarily have to have shapes that reflect prescription values for a wearer. Note that "a near-vision power that corresponds to a near distance" referred to in the present specification includes a power that causes light to converge in front of the retina as well as the "near-vision power for seeing a near distance", which is the expression used heretofore, i.e., a power that corresponds to a prescription value for a wearer. This may also be referred to as "a power that corresponds to a near distance" to avoid misinterpretation.

As a result of the above, according to each example of the present embodiment, when the lens is viewed from the center toward the periphery, it is possible to immediately reduce a cylinder power generated in the intermediate portion to make the cylinder power small in the far-vision portion or the near-vision portion provided along the outer edge of the intermediate portion, and consequently, it is possible to secure a wide region in which the cylinder power is small in the far-vision portion or the near-vision portion provided along the outer edge of the intermediate portion.

2. Design Method (Manufacturing Method) for Contact Lens

The contents described above are fully applicable to a design method and a manufacturing method for a contact lens. For example, the design method has the following configuration.

A method for designing an ophthalmic lens that includes an optical portion that includes a near-vision portion having a near-vision power that corresponds to a near distance, a far-vision portion having a far-vision power that corresponds to a distance that is farther than the near distance, and an annular intermediate portion that connects the near-vision portion and the far-vision portion to each other, the near-vision portion or the far-vision portion being arranged at the center, the near-vision portion or the far-vision portion that is not arranged at the center being arranged in a ring shape along an outer edge of the intermediate portion, the method including designing the ophthalmic lens such that the intermediate portion includes a portion A in which a power is strengthened and thereafter weakened when the lens is viewed in an X direction from the center toward the periphery, and the intermediate portion includes a portion A' in which the power is strengthened and thereafter weakened when the lens is viewed in an X' direction from the center toward the periphery, the X' direction being exactly opposite to the X direction, the power being strengthened in the portion A and the portion A' to be stronger than the far-vision power of the far-vision portion that is arranged in the ring shape along the outer edge of the intermediate portion or the near-vision power of the near-vision portion that is arranged in the ring shape along the outer edge of the intermediate portion.

Note that a known method and a known device for designing a lens can be used in a specific procedure for designing the lens. Also, the cases (the case where the near-vision portion is arranged at the center and the case where the far-vision portion is arranged at the center) and the preferable examples described in "1. Contact lens" can be applied to this section, and descriptions thereof overlap descriptions in "1. Contact lens" and therefore are omitted here.

The manufacturing method includes a design step of designing an ophthalmic lens using the above-described method for designing an ophthalmic lens (combining preferable examples as appropriate depending on situations) and a processing step of manufacturing the designed ophthalmic lens using a processing device. Note that a known device for processing a lens can be used in a specific procedure for processing the lens.

3. Intraocular Lens (IOL) and Design Method (Manufacturing Method) for the Same

The technical idea of the present invention is fully applicable to an intraocular lens (IOL) and a design method (manufacturing method) for the same. There is no particular limitation on the intraocular lens, and the technical idea of the present invention is applicable to an intraocular lens of a type (in-the-bag) that is arranged inside of a lens capsule, an intraocular lens of a type (out-of-the-bag) that is arranged outside of the capsule, and an intraocular lens that is sewn, for example.

Note that, in a case where the technical idea of the present invention is applied to an intraocular lens, the intraocular lens only needs to include at least the optical portion. Although an annular peripheral portion may also be provided along the peripheral edge of the optical portion that mainly contributes to optical performance as described in "1-1. Multifocal contact lens (multifocal lens)", an intraocular lens in this example is constituted by the optical portion and a support portion that supports the optical portion in a lens capsule. In relatively many cases, an intraocular lens includes the optical portion described above and a support portion that extends from the optical portion. The shape of a support portion of a known intraocular lens can be adopted for the support portion, and the intraocular lens may also be provided with two support portions that extend like arms from the optical portion, for example.

As for a design method (manufacturing method) for the intraocular lens, a description of design of the optical portion is omitted because the description is similar to that in "2. Design method (manufacturing method) for contact lens". A known design method (processing device) for an intraocular lens can be used in a specific procedure for designing (manufacturing) the intraocular lens. Also, the cases (the case where the near-vision portion is arranged at the center and the case where the far-vision portion is arranged at the center) and the preferable examples described in "1. Contact lens" can be applied to this section, and descriptions thereof overlap descriptions in "1. Contact lens" and therefore are omitted here.

4. Ophthalmic Lens Set

The contents described above are fully applicable to a contact lens set that includes a plurality of contact lenses described in the present embodiment and an intraocular lens set that includes a plurality of intraocular lenses described in the present embodiment. These lens sets will be collectively referred to as "ophthalmic lens sets".

At least when contact lenses are sold as products, not only the contact lenses are sold one by one, but also a plurality of contact lenses that have various powers and base curves (e.g., a plurality of contact lenses that have the same base curve and different powers) are frequently collectively sold under the same product name.

Accordingly, the technical idea of the present invention is fully reflected in an ophthalmic lens set that includes a plurality of ophthalmic lenses of which the power shows behavior such as that described above in detail with respect to the contact lens (or the intraocular lens, etc.) according to the present embodiment.

From a different point of view, powers of all ophthalmic lens sets that constitute an ophthalmic lens set according to the present embodiment show the above-described behavior. This means that, even if an ophthalmic lens of which the power shows the above-described behavior is manufactured with a conventional technology, the ophthalmic lens set according to the present embodiment completely differs in the configuration from the accidentally manufactured ophthalmic lens.

The ophthalmic lens set including the plurality of ophthalmic lenses described above has the following configuration. Note that the preferable examples described above may also be combined with the following configuration as appropriate.

An ophthalmic lens set that includes a plurality of ophthalmic lenses each including an optical portion that includes a near-vision portion having a near-vision power that corresponds to a near distance, a far-vision portion having a far-vision power that corresponds to a distance that is farther than the near distance, and an annular intermediate portion that connects the near-vision portion and the far-vision portion to each other, the near-vision portion or the far-vision portion being arranged at the center, the near-vision portion or the far-vision portion that is not arranged at the center being arranged in a ring shape along an outer edge of the intermediate portion, wherein the intermediate portion includes a portion A in which a power is strengthened and thereafter weakened when the lens is viewed in an X direction from the center toward the periphery, and the intermediate portion includes a portion A' in which the power is strengthened and thereafter weakened when the lens is viewed in an X' direction from the center toward the periphery, the X' direction being exactly opposite to the X direction, the power being strengthened in the portion A and the portion A' to be stronger than the far-vision power of the far-vision portion that is arranged in the ring shape along the outer edge of the intermediate portion or the near-vision power of the near-vision portion that is arranged in the ring shape along the outer edge of the intermediate portion.

5. Variations

The present invention is not limited to the examples described above, and the examples and the preferable examples described above can of course be combined as appropriate.

In the embodiment described above, portions in which the power is strengthened and thereafter weakened are provided in both of the X direction and the X' direction, but it is expected that the effects of the present invention can be achieved to a certain extent even if such a portion is provided in only one of the directions. This is defined as follows.

An ophthalmic lens, a design method, or a manufacturing method for the same, the ophthalmic lens including an optical portion that includes a near-vision portion having a near-vision power that corresponds to a near distance, a far-vision portion having a far-vision power that corresponds to a distance that is farther than the near distance, and an annular intermediate portion that connects the near-vision portion and the far-vision portion to each other, the near-vision portion or the far-vision portion being arranged at the center, the near-vision portion or the far-vision portion that is not arranged at the center being arranged in a ring shape along an outer edge of the intermediate portion, wherein the far-vision portion or the near-vision portion that is arranged in the ring shape along an outer edge of a center portion of the optical portion includes a portion A in which a power is strengthened and thereafter weakened when the lens is viewed in an X direction from the center toward the periphery, and includes an inflection point of the power when the lens is viewed in an X' direction from the center toward the periphery, the X' direction being exactly opposite to the X direction.

Here, the inflection point of the power is provided in the X' direction because the effects of the present invention can be more easily achieved if the shape of the lens in the X' direction is not the same as but is close to a shape with which the power is strengthened and thereafter weakened. Such a shape is defined using the expression "includes an inflection point of the power".

Also, as described as the findings of the present invention, with the configurations described above, it is possible to make the curvature in the circumferential direction close to the curvature in the radial direction before the far-vision portion or the near-vision portion arranged along the outer edge. The effects of the present invention can also be achieved giving focus on this point. When focus is given on this point, the invention has the following configuration.

An ophthalmic lens including an optical portion that includes a near-vision portion having a near-vision power that corresponds to a near distance, a far-vision portion having a far-vision power that corresponds to a distance that is farther than the near distance, and an annular intermediate portion that connects the near-vision portion and the far-vision portion to each other, the near-vision portion or the far-vision portion being arranged at the center, the near-vision portion or the far-vision portion that is not arranged at the center being arranged in a ring shape along an outer edge of the intermediate portion, wherein in the intermediate portion, a curvature in a circumferential direction is made closer to a curvature in a radial direction when the lens is viewed in an X direction from the center toward the periphery, and the curvature in the circumferential direction is made closer to the curvature in the radial direction when the lens is viewed in an X' direction from the center toward the periphery, the X' direction being exactly opposite to the X direction.

Also, as described as the findings of the present invention, with the configurations described above, it can be ensured that a cylinder power generated in the intermediate portion immediately decreases when the lens is viewed from the center toward the periphery (in the X direction and the X' direction). The effects of the present invention can also be achieved giving focus on this point. When focus is given on this point, the invention has the following configuration.

An ophthalmic lens including an optical portion that includes a near-vision portion having a near-vision power that corresponds to a near distance, a far-vision portion having a far-vision power that corresponds to a distance that is farther than the near distance, and an annular intermediate portion that connects the near-vision portion and the far-vision portion to each other, the near-vision portion or the far-vision portion being arranged at the center, the near-vision portion or the far-vision portion that is not arranged at the center being arranged in a ring shape along an outer edge of the intermediate portion, wherein in a case where the far-vision portion is arranged in the ring shape along the outer edge of the intermediate portion in the optical portion, a cylinder power (unit: diopter) satisfies the following condition 1 when the lens is viewed in an X direction from the center toward the periphery and an X' direction from the center toward the periphery, the X' direction being exactly opposite to the X direction, cylinder power at a point at which the power reaches the far-vision power as a result of being weakened after being strengthened for far vision to be stronger than the far-vision power in the intermediate portion≤0.30 D, and     Condition 1 in a case where the near-vision portion is arranged in the ring shape along the outer edge of the intermediate portion in the optical portion, the cylinder power satisfies the following condition 2 when the lens is viewed in the X direction and the X' direction, cylinder power at a point at which the power reaches the near-vision power as a result of being weakened after being strengthened for near vision to be stronger than the near-vision power in the intermediate portion≤0.30 D.     Condition 2

The conditions 1 and 2 in this configuration may also be replaced with the following conditions 1' and 2' or the following conditions 1' and 2' may also be added to the conditions 1 and 2.

[cylinder power at a point at which the power reaches the far-vision power as a result of being weakened after being strengthened for far vision to be stronger than the far-vision power in the intermediate portion]/[maximum cylinder power in the intermediate portion]≤0.30     Condition 1'

[cylinder power at a point at which the power reaches the near-vision power as a result of being weakened after being strengthened for near vision to be stronger than the near-vision power in the intermediate portion]/[maximum cylinder power in the intermediate portion] ≤0.30     Condition 2'

REFERENCE SIGNS LIST

1 Near-vision portion
2 Far-vision portion
3 Intermediate portion
4 Optical portion
5 Peripheral portion
6 Multifocal contact lens

The invention claimed is:

1. An ophthalmic lens comprising:
an optical portion that includes
  a near-vision portion having a near-vision spherical power for seeing a near distance,
  a far-vision portion having a far-vision spherical power for seeing a distance that is farther than the near distance, and
  an annular intermediate portion that connects the near-vision portion and the far-vision portion to each other, the near-vision portion or the far-vision portion being arranged at the center, the near-vision portion or the far-vision portion that is not arranged at the center being arranged in a ring shape along an outer edge of the intermediate portion, wherein
the intermediate portion includes
  a portion A in which a spherical power is strengthened and thereafter weakened when the lens is viewed in an X direction from the center toward the periphery, and
  a portion A' in which the spherical power is strengthened and thereafter weakened when the lens is viewed in an X' direction from the center toward the periphery, the X' direction being exactly opposite to the X direction,
    (i) the spherical power being strengthened for far vision to be stronger than the far-vision spherical power of the far-vision portion and thereafter weakened to reach the far-vision spherical power in the X direction in the portion A and in the X' direction in the portion A' when the far-vision portion is arranged in the ring shape along the outer edge of the intermediate portion or
    (ii) the spherical power being strengthened for near vision to be stronger than the near-vision spherical power of the near-vision portion and thereafter weakened to reach the near-vision spherical power in the direction in the portion A and in the X' direction the portion A' when the near-vision portion is arranged in the ring shape along the outer edge of the intermediate portion.

2. The ophthalmic lens according to claim 1, wherein
in the optical portion, the far-vision portion is arranged in the ring shape along the outer edge of the intermediate portion, and
the lens has a shape with which the spherical power, in the intermediate portion, is strengthened for far vision to be stronger than the far-vision spherical power and thereafter weakened to reach the far-vision spherical power in the X direction in the portion A and in the X' direction in the portion A'.

3. The ophthalmic lens according to claim 2, wherein
when the lens is viewed in the X direction and the X' direction, a cylinder power (unit: diopter) satisfies the following conditions, cylinder power at a point at which the spherical power is strengthened for far vision to be stronger than the far-vision spherical power and thereafter weakened to reach the far-vision spherical power in the portion A is ≤0.30 D, and     Condition 1-1 cylinder power at a point at which the spherical power is strengthened for far vision to be stronger than the far-vision spherical power and thereafter weakened to reach the far-vision spherical power in the portion A' is ≤0.30 D.     Condition 2-1

4. The ophthalmic lens according to claim 2, wherein
a ratio of (i) a difference between the local minimum spherical power value in the portion A and the far-vision spherical power, or a difference between the local minimum spherical power value in the portion A' and the far-vision spherical power to (ii) a difference between the near-vision spherical power and the far-vision spherical power is at least 0.15 and no greater than 1.0.

5. The ophthalmic lens according to claim 1, wherein
in the optical portion, the near-vision portion is arranged in the ring shape along the outer edge of the intermediate portion, and
the lens has a shape with which the spherical power, in the intermediate portion is strengthened for near vision to be stronger than the near-vision spherical power and thereafter weakened to reach the near-vision spherical power in the X direction in the portion A and in the X' direction in the portion A'.

6. The ophthalmic lens according to claim 5, wherein
when the lens is viewed in the X direction and the X' direction, a cylinder power (unit: diopter) satisfies the following conditions, cylinder power at a point at which the spherical power is strengthened for near vision to be stronger than the near-vision spherical power and thereafter weakened to reach the near-vision spherical power in the portion A is ≤0.30 D, and     Condition 1-2 cylinder power at a point at which the spherical power is strengthened for near vision to be stronger than the near-vision spherical and thereafter weakened to reach the near-vision spherical power in the portion A' is ≤0.30 D.     Condition 2-2

7. The ophthalmic lens according to claim 5, wherein
a ratio of (i) a difference between the local maximum spherical power value in the portion A and the far-vision spherical power, or a difference between the local maximum spherical power value in the portion A' and the near-vision spherical power to (ii) a difference between the near-vision spherical power and the far-vision spherical power is at least 0.15 and no greater than 1.0.

8. The ophthalmic lens according to claim 1, wherein
the near-vision portion or the far-vision portion that is arranged at the center is provided so as to include an optical center of the ophthalmic lens.

9. The ophthalmic lens according to claim 1, wherein
the ophthalmic lens is a contact lens.

10. The ophthalmic lens according to claim 1, wherein
the ophthalmic lens is an intraocular lens.

11. A method for manufacturing an ophthalmic lens that includes
an optical portion that includes a near-vision portion having a near-vision spherical power for seeing a near distance,
a far-vision portion having a far-vision spherical power for seeing a distance that is farther than the near distance, and
an annular intermediate portion that connects the near-vision portion and the far-vision portion to each other, the near-vision portion or the far-vision portion being arranged at the center, the near-vision portion or the far-vision portion that is not arranged at the center being arranged in a ring shape along an outer edge of the intermediate portion, the method for manufacturing comprising:
forming the ophthalmic lens such that the intermediate portion includes a portion A in which a spherical power is strengthened and thereafter weakened when the lens is viewed in an X direction from the center toward the periphery, and
a portion A' in which the spherical power is strengthened and thereafter weakened when the lens is viewed in an X' direction from the center toward the periphery, the X' direction being exactly opposite to the X direction,
(i) the spherical power being strengthened for far vision to be stronger than the far-vision spherical power of the far-vision portion and thereafter weakened to reach the far-vision spherical power in the X direction in the portion A and in the X' direction in the portion A' when the far-vision portion is arranged in the ring shape along the outer edge of the intermediate portion or
(ii) the spherical power being strengthened for near vision to be stronger than the near-vision spherical power of the near-vision portion and thereafter weakened to reach the near-vision spherical power in the X direction in the portion A and in the X' direction the portion A' when the near-vision portion is arranged in the ring shape along the outer edge of the intermediate portion.

12. The method for manufacturing an ophthalmic lens according to claim 11, wherein
in the optical portion, the far-vision portion is arranged in the ring shape along the outer edge of the intermediate portion, and
the ophthalmic lens is formed such that the spherical power, in the intermediate portion, is strengthened for far vision to be stronger than the far-vision spherical power and thereafter weakened to reach the far-vision spherical power in the X direction in the portion A and in the X' direction in the portion A'.

13. The method for manufacturing an ophthalmic lens according to claim 12, wherein
when the lens is viewed in the X direction and the X' direction, a cylinder power (unit: diopter) satisfies the following conditions, cylinder power at a point at which the spherical power is strengthened for far vision to be stronger than the far-vision spherical power and thereafter weakened to reach the far-vision spherical power in the portion A is ≤0.30 D,     Condition 1-1 cylinder power at a point at which the spherical power is strengthened for far vision to be stronger than the far-vision spherical power and thereafter weakened to reach the far-vision spherical power in the portion A' is ≤0.30 D.     Condition 2-1

14. The method for manufacturing an ophthalmic lens according to claim 12, wherein
a ratio of (i) a difference between the local minimum spherical power value in the portion A and the far-vision spherical power, or a difference between the local minimum spherical power value in the portion A' and the far-vision spherical power to (ii) a difference between the near-vision spherical power and the far-vision spherical power is at least 0.15 and no greater than 1.0.

15. The method for manufacturing an ophthalmic lens according to claim 11, wherein
in the optical portion, the near-vision portion is arranged in the ring shape along the outer edge of the intermediate portion, and the ophthalmic lens is formed such that the spherical power, in the intermediate portion, is strengthened for near vision to be stronger than the near-vision spherical power and thereafter weakened to reach the near-vision spherical power in the X direction in the portion A and in the X' direction in the portion A'.

16. The method for manufacturing an ophthalmic lens according to claim 15, wherein
when the lens is viewed in the X direction and the X' direction, a cylinder power (unit: diopter) satisfies the following conditions, cylinder power at a point at which the spherical power is strengthened for near vision to be stronger than the near-vision spherical power and thereafter weakened to reach the near-vision spherical power in the portion A is ≤0.30 D, and            Condition 1-2 cylinder power at a point at which the spherical power is strengthened for near vision to be stronger than the near-vision spherical power and thereafter weakened to reach the near-vision spherical power in the portion A' is ≤0.30 D.            Condition 2-2

17. The method for manufacturing an ophthalmic lens according to claim 15, wherein
a ratio of (i) a difference between the local maximum spherical power value in the portion A and the far-vision spherical power or a difference between the local maximum spherical power value in the portion A' and the near-vision spherical power to (ii) a difference between the near-vision spherical power and the far-vision spherical power is at least 0.15 and no greater than 1.0.

18. The method for manufacturing an ophthalmic lens according to claim 11, wherein
the near-vision portion or the far-vision portion that is arranged at the center is provided so as to include an optical center of the ophthalmic lens.

19. The method for manfacturing an ophthalmic lens according to claim 11, wherein
the ophthalmic lens is a contact lens.

20. The method for manufacturing an ophthalmic lens according to claim 11, wherein
the ophthalmic lens is an intraocular lens.

21. An ophthalmic lens set comprising a plurality of ophthalmic lenses that each include an optical portion that includes
a near-vision portion having a near-vision spherical power for seeing a near distance,
a far-vision portion having a far-vision spherical power for seeing a distance that is farther than the near distance, and
an annular intermediate portion that connects the near-vision portion and the far-vision portion to each other, the near-vision portion or the far-vision portion being arranged at the center, the near-vision portion or the far-vision portion that is not arranged at the center being arranged in a ring shape along an outer edge of the intermediate portion, wherein
the intermediate portion includes
a portion A in which a spherical power is strengthened and thereafter weakened when the lens is viewed in an X direction from the center toward the periphery, and
a portion A' in which the spherical power is strengthened and thereafter weakened when the lens is viewed in an X' direction from the center toward the periphery, the X' direction being exactly opposite to the X direction,
(i) the spherical power being strengthened for far vision to be stronger than the far-vision spherical power of the far-vision portion and thereafter weakened to reach the far-vision spherical power in the direction in the portion A and in the X' direction in the portion A' when the far-vision portion is arranged in the ring shape along the outer edge of the intermediate portion or
(ii) the spherical power being strengthened for near vision to be stronger than the near-vision power of the near-vision portion and thereafter weakened to reach the near-vision spherical power in the X direction in the portion A and in the X' direction the portion A' when the near-vision portion is arranged in the ring shape along the outer edge of the intermediate portion.

22. An ophthalmic lens set comprising a plurality of ophthalmic lenses that each include an optical portion that includes
a near-vision portion having a near-vision spherical power for seeing a near distance,
a far-vision portion having a far-vision spherical power for seeing a distance that is farther than the near distance, and
an annular intermediate portion that connects the near-vision portion and the far-vision portion to each other, the near-vision portion or the far-vision portion being arranged at the center, the near-vision portion or the far-vision portion that is not arranged at the center being arranged in a ring shape along an outer edge of the intermediate portion, wherein
the intermediate portion includes
a portion A in which a spherical power is strengthened and thereafter weakened when the lens is viewed in an X direction from the center toward the periphery, and
a portion A' in which the spherical power is strengthened and thereafter weakened when the lens is viewed in an X' direction from the center toward the periphery, the X' direction being exactly opposite to the X direction,
(i) the spherical power being strengthened for far vision to be stronger than the far-vision spherical power of the far-vision portion and thereafter weakened to reach the far-vision spherical power in the X direction in the portion A and in the X' direction in the portion A' when the far-vision portion is arranged in the ring shape along the outer edge of the intermediate portion or
(ii) the spherical power being strengthened for near vision to be stronger than the near-vision spherical power of the near-vision portion and thereafter weakened to reach the near-vision spherical power in the X direction in the portion A and in the X' direction the portion A' when the near-vision portion is arranged in the ring shape along the outer edge of the intermediate portion, wherein
when the lens is viewed in the X direction and the X' direction, a cylinder power (unit: diopter) satisfies the following conditions, cylinder power at a point at which the spherical power is strengthened for near-vision to be stronger than the near-vision spherical power and thereafter weakened to reach the near-vision spherical power in the portion A is ≤0.30 D, and          Condition 1-2 cylinder power at a point at which the spherical power is strengthened for near-vision to be stronger than the near-vision spherical power and thereafter weakened to reach the near-vision spherical power in the portion A' is ≤0.30 D.          Condition 2-2

* * * * *